(12) United States Patent
Akbarali et al.

(10) Patent No.: US 9,776,970 B2
(45) Date of Patent: Oct. 3, 2017

(54) BOSUTINIB FORMS AND PREPARATION METHODS THEREOF

(71) Applicant: Apotex Inc., Toronto (CA)

(72) Inventors: Padiyath Mohammed Akbarali, Bangalore (IN); Venkata Ramana Kintali, Bangalore (IN); Heggadde Nanjunda Bhatta Shreenivasa Murthy, Bangalore (IN); Girisha Meenkere, Chitradurga (IN); Somanath Bhupal Venkata, Kurnool (IN); Raja Ramesh Manda, East Godavari (IN); Vishal Amrutlal Sodha, Rajkot (IN); Abbulu Kante, Bangalore (IN)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 15/120,226

(22) PCT Filed: Feb. 20, 2015

(86) PCT No.: PCT/CA2015/000100
§ 371 (c)(1),
(2) Date: Aug. 19, 2016

(87) PCT Pub. No.: WO2015/123758
PCT Pub. Date: Aug. 27, 2015

(65) Prior Publication Data
US 2017/0057923 A1     Mar. 2, 2017

(30) Foreign Application Priority Data
Feb. 20, 2014   (IN) .......................... 0840/CHE/2014

(51) Int. Cl.
| | |
|---|---|
| C07D 401/12 | (2006.01) |
| A61K 31/496 | (2006.01) |
| C07D 215/54 | (2006.01) |
| A61K 31/4706 | (2006.01) |
| A61K 9/14 | (2006.01) |

(52) U.S. Cl.
CPC ............ C07D 215/54 (2013.01); A61K 9/146 (2013.01); A61K 31/4706 (2013.01)

(58) Field of Classification Search
CPC ............................ C07D 401/12; A61K 31/496
USPC .......................................... 544/363; 514/253
See application file for complete search history.

(56) References Cited

U.S. PATENT DOCUMENTS

| | | |
|---|---|---|
| 6,002,008 A | 12/1999 | Wissner et al. |
| RE42,376 E | 5/2011 | Wissner et al. |
| 2003/0212276 A1 | 11/2003 | Boschelli et al. |
| 2004/0229880 A1 | 11/2004 | Boschelli et al. |
| 2005/0043537 A1 | 2/2005 | Sutherland et al. |
| 2005/0101780 A1 | 5/2005 | Boschelli et al. |
| 2007/0015767 A1 | 1/2007 | Tesconi et al. |

FOREIGN PATENT DOCUMENTS

| | | |
|---|---|---|
| CA | 2613053 A1 | 1/2007 |
| CN | 101792416 A | 8/2010 |
| CN | 103265482 A | 8/2013 |
| WO | 03093241 A1 | 11/2003 |
| WO | 2004075898 A1 | 9/2004 |
| WO | 2005019201 A2 | 3/2005 |
| WO | 2005047259 A1 | 5/2005 |

OTHER PUBLICATIONS

Boschelli et al.; "7-Alkoxy-4-phenylamino-3-quinolinecarbonitriles as Dual Inhibitors of Src and Abl Kinases"; J. Med. Chem.; 2004; pp. 1599-1601; vol. 47.
Boschelli et al.; "Inhibition of Src Kinase Activity by 4-Anilino-5,10-dihydropyrimido[4,5-b]quinolines"; Bioorganic & Medicinal Chemistry Letters; 2003; pp. 2977-2980; vol. 13.
Boschelli et al.; "Optimization of 4-Phenylamino-3-quinolinecarbonitriles as Potent Inhibitors of Src Kinase Activity"; J. Med. Chem.; 2001; pp. 3965-3977; vol. 44.
Withbroe et al.; "A Robust, Streamlined Approach to Bosutinib Monohydrate"; Org. Process Res. Dev.; 2013; pp. 500-504; vol. 17.
Yin et al.; "Synthesis of Bosutinib from 3-Methoxy-4-hydroxybenzoic Acid"; Molecules; 2010; pp. 4261-4266; vol. 15.

*Primary Examiner* — Charanjit Aulakh
(74) *Attorney, Agent, or Firm* — The Webb Law Firm

(57) ABSTRACT

The present subject matter relates to solvates and the amorphous form of bosutinib; the solvates namely being a propylene glycol solvate and an acetonitrile solvate. Also provided are processes for preparing the propylene glycol solvate, the amorphous form and the crystalline acetonitrile solvate of bosutinib; as well as compositions comprising said forms. Bosutinib is a 3-quinolinecarbonitrile kinase inhibitor and is indicated for the treatment of adult patients with chronic, accelerated, or blast phase Ph+ chronic myelogenous leukemia (CMS) with resistance or intolerance to prior therapy.

11 Claims, 13 Drawing Sheets

BOSUTINIB FORMS AND PREPARATION METHODS THEREOF

CROSS-REFERENCE TO RELATED APPLICATIONS

This application is the United States national phase of International Application No. PCT/CA2015/000100 filed Feb. 20, 2015, and claims priority to Indian Patent Application No. 0840/CHE/2014 filed Feb. 20, 2014, the disclosures of which are hereby incorporated in their entirety by reference.

TECHNICAL FIELD

The present invention relates to Bosutinib forms, pharmaceutical compositions thereof and processes for preparation thereof.

BACKGROUND

Bosutinib, a kinase inhibitor, chemically known as, 4-[(2,4-dichloro-5-methoxyphenyl)amino]-6-methoxy-7-[3-(4-methyl-1-piperazinyl) propoxy]-3-quinolinecarbonitrile. Bosutinib can be structurally represented as follows:

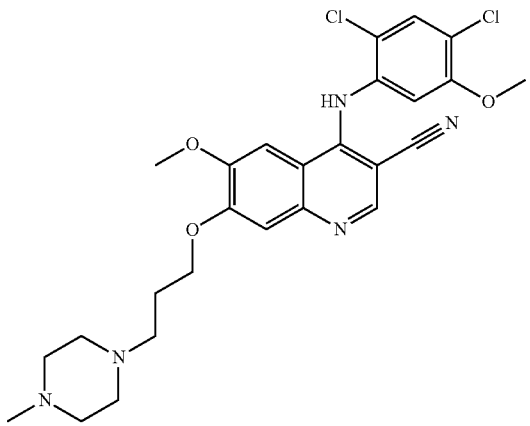

Bosutinib is the active pharmaceutical ingredient in the BOSULIF™ tablets available for oral administration, indicated for the treatment of adult patients with chronic, accelerated, or blast phase Ph+ chronic myelogenous leukemia (CML) with resistance or intolerance to prior therapy.

U.S. Pat. No. 6,002,008 provides compounds having the formula:

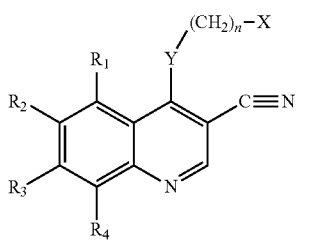

wherein: X is cycloalkyl which may be optionally substituted; or is a pyridinyl, pyrimidinyl, or phenyl ring; wherein the pyridinyl, pyrimidinyl, or phenyl ring may be optionally substituted; n is 0-1; Y is —NH—, —O—, —S—, or —NR—; R is alkyl of 1-6 carbon atoms; $R_1$, $R_2$, $R_3$, and $R_4$ are each, independently, hydrogen, halogen, alkyl, alkenyl, alkynyl, alkenyloxy, alkynyloxy, hydroxymethyl, halomethyl, alkanoyloxy, alkenoyloxy, alkynoyloxy, alkenoyloxymethyl, alkenoyloxymethyl, alkynoyloxymethyl, alkoxymethyl, alkoxy, alkylthio, alkylsulphinyl, alkylsulphonyl, alkylsulfonamido, alkenylsulfonamido, alkynylsulfonamido, hydroxy, trifluoromethyl, cyano, nitro, carboxy, carboalkoxy, carboalkyl, phenoxy, phenyl, thiophenoxy, benzyl, amino, hydroxyamino, alkoxyamino, alkylamino, dialkylamino, aminoalkyl, N-alkylaminoalkyl, N,N-dialkylaminoalkyl, phenylamino, benzylamino, $R_5$—CONH(CH$_3$)$_p$—,

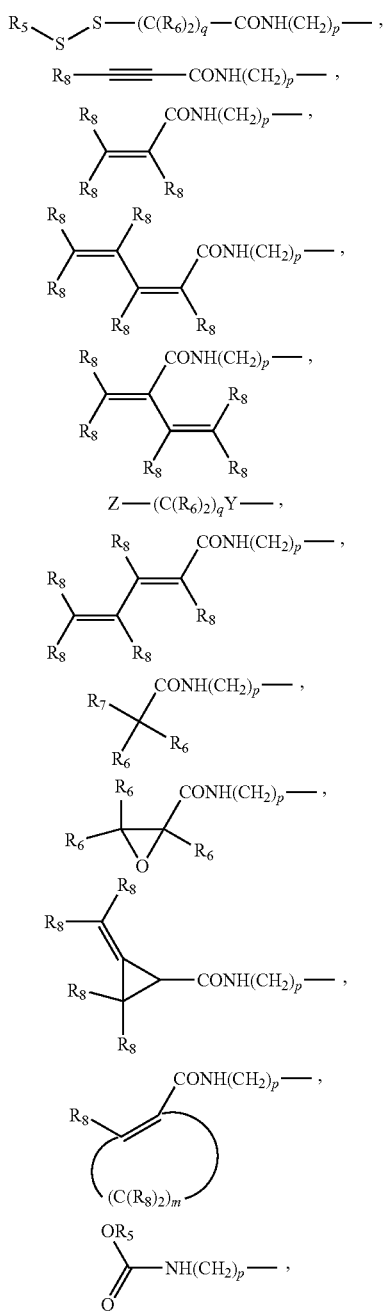

-continued

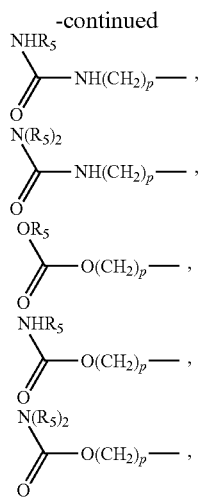

$R_5$ is alkyl which may be optionally substituted, or phenyl which may be optionally substituted; $R_6$ is hydrogen, alkyl, or alkenyl; $R_7$ is chloro or bromo $R_8$ is hydrogen, alkyl, aminoalkyl, N-alkylaminoalkyl, N,N-dialkylaminoalkyl, N-cycloalkylaminoalkyl, N-cycloalkyl-N-alkylaminoalkyl, N,N-dicycloalkylaminoalkyl, morpholino-N-alkyl, piperidino-N-alkyl, N-alkyl-piperidino-N-alkyl, azacycloalkyl-N-alkyl, hydroxyalkyl, alkoxyalkyl, carboxy, carboalkoxy, phenyl, carboalkyl+, chloro, fluoro, or bromo; Z is amino, hydroxy, alkoxy, alkylamino, dialkylamino, morpholino, piperazino, N-alkylpiperazino, or pyrrolidino; m=1-4, q=1-3, and p=0-3; any of the substituents $R_1$, $R_2$, $R_3$, or $R_4$ that are located on contiguous carbon atoms can together be the divalent radical —O—C($R_8$)$_2$—O—; or a pharmaceutically acceptable salt thereof with the proviso that when Y is —NH—, $R_1$, $R_2$, $R_3$, and $R_4$ are hydrogen, and n is 0, X is not 2-methylphenyl, which are inhibitors of protein tyrosine kinase.

U.S. RE 42,376 provides compounds of formula I having the structure:

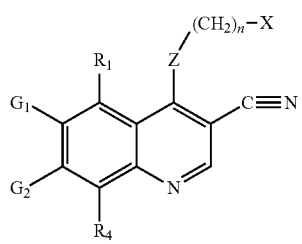

I wherein $G_1$, $G_2$, $R_1$, $R_4$, Z, n, and X are defined in the specification or a pharmaceutically acceptable salt thereof which are useful as antineoplastic agents and in the treatment of polycystic kidney disease.

SUMMARY

This invention is based, at least in part, on solid forms of Bosutinib. In particular, a propylene glycol solvate of Bosutinib, an amorphous form of Bosutinib, a solid dispersion comprising an amorphous form of Bosutinib and a crystalline acetonitrile solvate of Bosutinib are provided in the present invention. Also provided are methods of preparation thereof and pharmaceutical formulations comprising the solid forms of Bosutinib.

In illustrative embodiments of the present invention, there is provided a propylene glycol solvate of Bosutinib.

In illustrative embodiments of the present invention, there is provided a crystalline propylene glycol solvate of Bosutinib characterized by a powder X-ray diffractogram (PXRD) comprising peaks, in terms of degrees 2-theta, at about 10.8±0.2°, 11.7±0.2°, 21.7±0.2°, and 23.6±0.2°.

In illustrative embodiments of the present invention, there is provided a crystalline propylene glycol solvate of Bosutinib described herein wherein the PXRD further comprises at least one peak, in terms of degrees 2-theta, selected from the group consisting of: 18.3±0.2°, 19.3±0.2°, 22.1±0.2°, and 26.3±0.2°.

In illustrative embodiments of the present invention, there is provided a crystalline propylene glycol solvate of Bosutinib described herein wherein the PXRD further comprises at least one peak, in terms of degrees 2-theta, selected from the group consisting of: 12.4±0.2°, 23.3±0.2°, 24.9±0.2°, and 27.5±0.2°.

In illustrative embodiments of the present invention, there is provided a crystalline propylene glycol solvate of Bosutinib described herein characterized by a PXRD substantially similar to the PXRD as illustrated in FIG. 12.

In illustrative embodiments of the present invention, there is provided a crystalline propylene glycol solvate of Bosutinib described herein characterized by a differential scanning calorimetry (DSC) thermogram substantially similar to the DSC thermogram as illustrated in FIG. 13.

In illustrative embodiments of the present invention, there is provided a process for preparing propylene glycol solvate of Bosutinib, the process comprising: a) providing a solution or suspension of Bosutinib or solvate thereof in propylene glycol, thereby forming a reaction mixture; b) maintaining the reaction mixture at a suitable temperature, thereby forming a maintained reaction mixture; and c) isolating the propylene glycol solvate of Bosutinib from the maintained reaction mixture.

In illustrative embodiments of the present invention, there is provided a process described herein wherein providing the solution or suspension of Bosutinib or solvate thereof in propylene glycol further comprises providing the solution or suspension in a suitable solvent.

In illustrative embodiments of the present invention, there is provided a process described herein wherein the suitable solvent is selected from the group consisting of: alcohols, esters, ketones, hydrocarbons, ethers, nitriles, amides, water, and mixtures of at least two thereof.

In illustrative embodiments of the present invention, there is provided a process described herein wherein the suitable solvent is selected from the group consisting of: methyl acetate, ethyl acetate, propyl acetate, isopropyl acetate, acetone, methyl ethyl ketone, methyl isobutyl ketone, and mixtures of at least two thereof.

In illustrative embodiments of the present invention, there is provided a pharmaceutical composition comprising propylene glycol solvate of Bosutinib described herein together with one or more pharmaceutically acceptable excipients, carriers or diluents.

In illustrative embodiments of the present invention, there is provided an amorphous form of Bosutinib.

In illustrative embodiments of the present invention, there is provided an amorphous form of Bosutinib described herein wherein the amorphous form is substantially pure.

In illustrative embodiments of the present invention, there is provided an amorphous form of Bosutinib described herein characterized by a PXRD substantially similar to the PXRD as illustrated in any one of FIG. 1, 3, or 5.

In illustrative embodiments of the present invention, there is provided an amorphous form of Bosutinib described herein characterized by a DSC thermogram substantially similar to the DSC thermogram as illustrated in any one of FIG. 2, 4, or 6.

In illustrative embodiments of the present invention, there is provided a process for preparing an amorphous form of Bosutinib, the process comprising: A) providing a solution of Bosutinib or solvate thereof in a solvent; and B) isolating the amorphous form of Bosutinib from the solution.

In illustrative embodiments of the present invention, there is provided a process described herein wherein the Bosutinib solvate is selected from the group consisting of: methanol, isopropanol, acetonitrile, and propylene glycol solvate.

In illustrative embodiments of the present invention, there is provided a process described herein wherein the solvent is selected from the group consisting of: alcohols, esters, ketones, hydrocarbons, ethers, nitriles, amides, water, and mixtures of at least two thereof.

In illustrative embodiments of the present invention, there is provided a process described herein wherein the solvent is selected from the group consisting of: methyl acetate, ethyl acetate, propyl acetate, isopropyl acetate, acetone, methyl ethyl ketone, methyl isobutyl ketone, and mixtures of at least two thereof.

In illustrative embodiments of the present invention, there is provided a process described herein wherein isolating comprises freeze drying, spray drying, thin film drying, or lyophilization.

In illustrative embodiments of the present invention, there is provided a pharmaceutical composition comprising an amorphous form of Bosutinib described herein together with one or more pharmaceutically acceptable excipients, carriers, or diluents.

In illustrative embodiments of the present invention, there is provided a solid dispersion comprising an amorphous form of Bosutinib together with one or more pharmaceutically acceptable excipients, carriers, or diluents.

In illustrative embodiments of the present invention, there is provided a solid dispersion described herein wherein the pharmaceutically acceptable carrier comprises one or more of copovidone, povidone, or Neusilin™.

In illustrative embodiments of the present invention, there is provided a process for the preparation of a solid dispersion comprising an amorphous form of Bosutinib in combination with one or more pharmaceutically acceptable carriers, the process comprising: i) providing, in a solvent, a solution or a suspension comprising Bosutinib or a solvate thereof and one or more pharmaceutically acceptable carriers; ii) either: ii-i) removing the solvent from the solution or suspension; or ii-ii) combining the solution with an anti-solvent; and iii) isolating the solid dispersion comprising an amorphous form of Bosutinib in combination with one or more pharmaceutically acceptable carriers.

In illustrative embodiments of the present invention, there is provided a process described herein wherein the Bosutinib solvate is selected from the group consisting of: methanol, isopropanol, acetonitrile, and propylene glycol solvate.

In illustrative embodiments of the present invention, there is provided a process described herein wherein the pharmaceutically acceptable carrier comprises one or more of povidone, copovidone, or Neusilin™.

In illustrative embodiments of the present invention, there is provided a process described herein wherein the solvent is selected from the group consisting of: alcohols, esters, ketones, hydrocarbons, ethers, nitriles, amides, water, and mixtures of at least two thereof.

In illustrative embodiments of the present invention, there is provided a process described herein wherein the solvent is selected from the group consisting of: methyl acetate, ethyl acetate, propyl acetate, isopropyl acetate, acetone, methyl ethyl ketone, methyl isobutyl ketone, and mixtures of at least two thereof.

In illustrative embodiments of the present invention, there is provided a process described herein wherein the removing the solvent comprises evaporating the solvent, distilling, spray drying, thin film drying, freeze drying, lyophilisation, or a combination thereof.

In illustrative embodiments of the present invention, there is provided a process described herein wherein the anti-solvent is selected from the group consisting of: aliphatic hydrocarbon liquids, alicyclic hydrocarbon liquids, aromatic hydrocarbon liquids, ethers, and mixtures of at least two thereof.

In illustrative embodiments of the present invention, there is provided a pharmaceutical composition comprising a solid dispersion comprising an amorphous form of Bosutinib together with one or more pharmaceutically acceptable excipients, carriers, or diluents.

In illustrative embodiments of the present invention, there is provided a crystalline acetonitrile solvate of Bosutinib.

In illustrative embodiments of the present invention, there is provided a crystalline acetonitrile solvate of Bosutinib described herein characterized by a PXRD comprising peaks, in terms of degrees 2-theta, at about $5.1\pm0.2°$, $14.1\pm0.2°$, $19.9\pm0.2°$, and $21.6\pm0.2°$.

In illustrative embodiments of the present invention, there is provided a crystalline acetonitrile solvate of Bosutinib described herein wherein the PXRD further comprises at least one peak, in terms of degrees 2-theta, selected from the group consisting of: $11.1\pm0.2°$, $12.0\pm0.2°$, $15.9\pm0.2°$, and $20.6\pm0.2°$.

In illustrative embodiments of the present invention, there is provided a crystalline acetonitrile solvate of Bosutinib described herein wherein the PXRD further comprises at least one peak, in terms of degrees 2-theta, at about $22.6\pm0.2°$, $24.2\pm0.2°$, $24.7\pm0.2°$, $25.9\pm0.2°$, and $28.4\pm0.2°$.

In illustrative embodiments of the present invention, there is provided a crystalline acetonitrile solvate of Bosutinib described herein characterized by a PXRD substantially similar to the PXRD as illustrated in FIG. 7.

In illustrative embodiments of the present invention, there is provided a crystalline acetonitrile solvate of Bosutinib described herein characterized by a DSC thermogram substantially similar to the DSC thermogram as illustrated in FIG. 8.

In illustrative embodiments of the present invention, there is provided a process for preparing a crystalline acetonitrile solvate of Bosutinib described herein, the process comprising: I) providing a solution or suspension of Bosutinib or solvate thereof in acetonitrile, thereby forming a reaction mixture; II) maintaining the reaction mixture at a suitable temperature, thereby forming a maintained reaction mixture; and III) isolating the crystalline acetonitrile solvate of Bosutinib from the maintained reaction mixture.

In illustrative embodiments of the present invention, there is provided a process described herein wherein isolating comprises decantation, centrifugation, gravity filtration, suction filtration, concentrating, cooling, stirring, shaking, adding seed crystals, evaporation, or rotational drying.

Other aspects and features of the present invention will become apparent to those ordinarily skilled in the art upon review of the following description of specific embodiments of the invention in conjunction with the accompanying figures.

DETAILED DESCRIPTION

Figure 1:
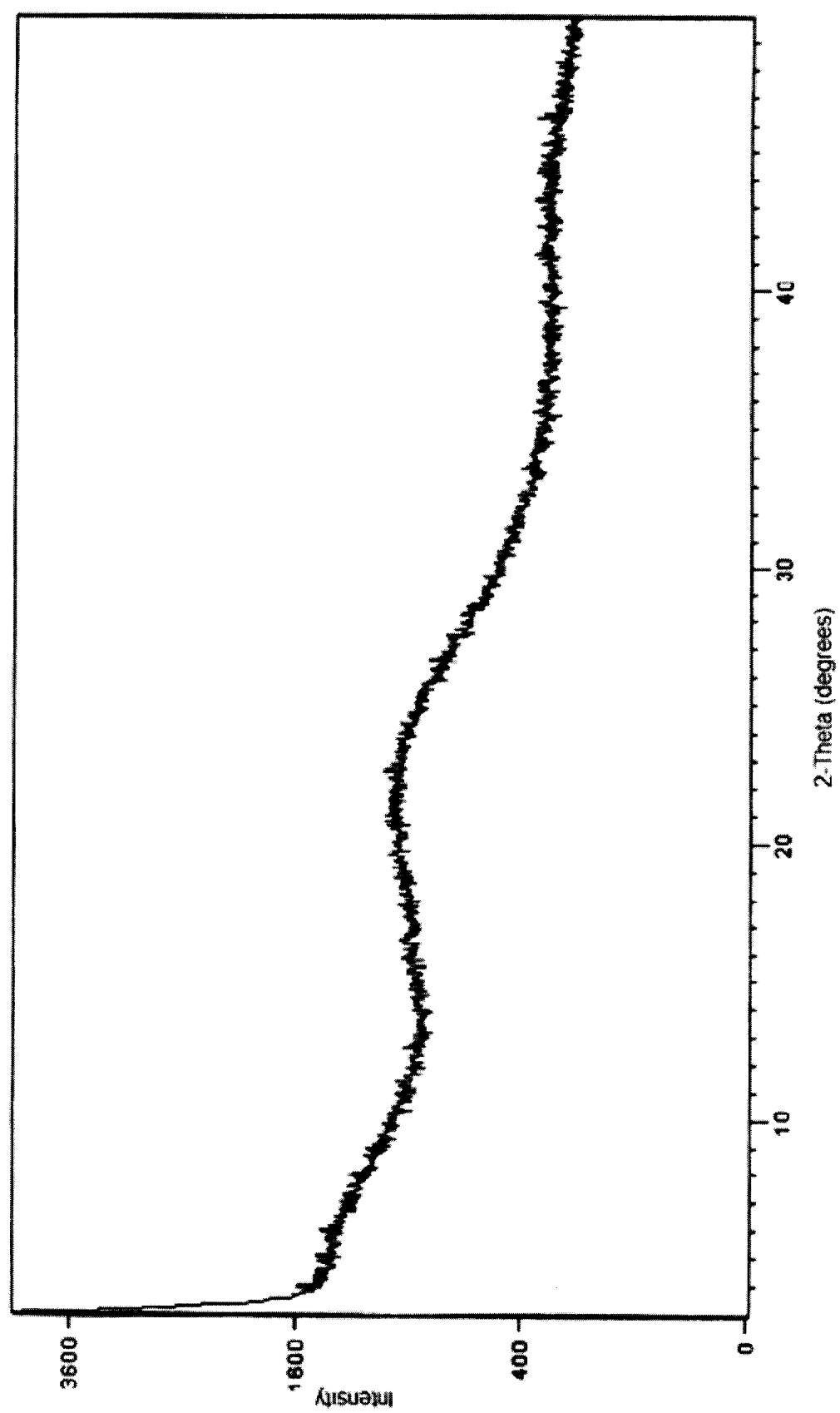
FIG. 1 is an illustration of a powder X-ray diffractogram (PXRD) of amorphous Bosutinib, prepared according to Example 5.

As used herein, an "alcohol" is an organic compound containing a carbon bound to a hydroxyl group. "$C_1$-$C_6$ alcohols" include, but are not limited to, methanol, ethanol, 2-nitroethanol, 2-fluoroethanol, 2,2,2-trifluoroethanol, ethylene glycol, 1-propanol, 2-propanol (isopropanol), 2-methoxyethanol, 1-butanol, 2-butanol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, phenol, glycerol, and the like.

As used herein, an "aliphatic hydrocarbon" is a liquid hydrocarbon compound, which may be linear, branched, or cyclic and may be saturated or have as many as two double bonds. A liquid hydrocarbon compound that contains a six-carbon group having three double bonds in a ring is called "aromatic." Examples of "$C_5$-$C_8$ aliphatic or aromatic hydrocarbons" include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, petroleum ethers, benzene toluene, ethylbenzene, m-xylene, o-xylene, p-xylene, trimethylbenzene, chlorobenzene, fluorobenzene, trifluorotoluene, and anisole.

As used herein, an "ester" is an organic compound containing a carboxyl group —(C═O)—O— bonded to two other carbon atoms. "$C_3$-$C_6$ esters" include, but are not limited to, ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, and the like.

As used herein, an "ether" is an organic compound containing an oxygen atom —O— bonded to two carbon atoms. "$C_2$-$C_6$ ethers" include, but are not limited to, diethyl ether, diisopropyl ether, methyl t-butyl ether, glyme, diglyme, tetrahydrofuran, 2-methyltetrahydrofuran, 1,4-dioxane, dibutyl ether, dimethylfuran, 2-methoxyethanol, 2-ethoxyethanol, anisole, and the like.

As used herein, a "hydrocarbon" is a liquid compound formed from carbon and hydrogen atoms, and may be linear, branched, cyclic, saturated, unsaturated, non-aromatic, or aromatic. Examples include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, petroleum ethers, benzene, toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, and the like.

As used herein, a "halogenated hydrocarbon" is an organic compound containing a carbon bound to a halogen. Halogenated hydrocarbons include, but are not limited to, dichloromethane, 1,2-dichloroethane, trichloroethylene, perchloroethylene, 1,1,1-trichloroethane, 1,1,2-trichloroethane, chloroform, carbon tetrachloride, and the like.

As used herein, a "ketone" is an organic compound containing a carbonyl group —(C═O)— bonded to two other carbon atoms. "$C_3$-$C_6$ ketones" include, but are not limited to, acetone, ethyl methyl ketone, diethyl ketone, methyl isobutyl ketone, ketones, and the like.

As used herein, a "nitrile" is an organic compound containing a cyano —(C≡N) bonded to another carbon atom. "$C_2$-$C_6$ nitriles" include, but are not limited to, acetonitrile, propionitrile, butanenitrile, and the like.

All percentages and ratios used herein are by weight of the total composition and all measurements made are at 25° C. and normal pressure unless otherwise designated.

All temperatures used herein are in degrees Celsius unless specified otherwise.

All ranges recited herein include the endpoints, including those that recite a range "between" two values.

As used herein, the term "anti-solvent" refers to a liquid that, when combined with a solution of Bosutinib, reduces solubility of the Bosutinib in the solution, causing crystallization or precipitation in some instances spontaneously, and in other instances with additional steps, such as seeding, cooling, scratching, and/or concentrating.

As used herein, "comprising" means the elements recited, or their equivalents in structure or function, plus any other element or elements that may or may not be recited. The terms "having" and "including" are also to be construed as open ended unless the context suggests otherwise. The terms "about," "substantially" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

The term "substantially pure" as used herein, when applied to the amorphous form of Bosutinib, means that greater than about 10% of the Bosutinib is amorphous, for example greater than about 20%, about 40%, greater than about 60%, greater than about 65%, greater than about 70%, greater than about 75%, greater than about 80%, greater than about 85%, greater than about 90%, greater than about 95%, greater than about 97.5%, greater than about 98%, greater than about 99%, or greater than about 99.5% of Bosutinib is amorphous.

Unless otherwise specified, Bosutinib as described herein also encompasses anhydrates, hydrates and solvates thereof.

Unless otherwise specified, the term "solvate(s)" as used herein, means compounds formed by solvation, for example as a combination of solvent molecules with molecules or ions of a solute. Well known solvent molecules include water, alcohols, nitriles, polar organic solvents etc.

Unless otherwise specified, the term "chemical purity" or "purity" as used herein refers to the purity with regard to unwanted residual solvents, reaction byproducts, impurities, and unreacted starting materials.

Unless otherwise specified, "pharmaceutically acceptable carriers" as used herein, that may be used for the preparation of solid dispersions of Bosutinib of the present invention include, but are not limited to: water soluble sugar derivatives including any pharmaceutically acceptable water soluble sugar excipients, preferably having low hygroscopicity, which include, but are not limited to, mannitol, lactose, fructose, sorbitol, xylitol, maltodextrin, dextrates, dextrins, lactitol, or the like; pharmaceutical hydrophilic carriers such as polyvinylpyrrolidones, gums, cellulose derivatives such as hydroxypropyl methylcelluloses, hydroxypropyl celluloses and microcrystalline celluloses, polymers of carboxymethyl celluloses, cyclodextrins, gelatins, hypromellose phthalates, sugars, polyhydric alcohols, polyethylene glycols, polyethylene oxides, polyoxyethylene derivatives, polyvinyl alcohols, propylene glycol derivatives, or the like; or organic amines such as primary, secondary, and tertiary alkyl amines, aromatic amines, alicyclic amines, cyclic amines, aralkyl amines, hydroxylamine or its derivatives, hydrazine or its derivatives, and guanidine or its derivatives; or copovidone, povidone and Neusilin™. The scope of the present invention without limitation includes, the use of mixtures of more than one of the pharmaceutical excipients to provide desired release profiles or for the enhancement of stability and also includes all viscosity grades, molecular weights, commercially available products, their copolymers and mixtures.

As used herein, the terms "optional" or "optionally" mean that the event or circumstance described in the specification may or may not occur, and that the description includes instances where the event occurs and instances where it does not.

As used herein when referring to a diffractogram, spectrum and/or to data presented in a graph, the term "peak" refers to a feature that one skilled in the art would recognize as not attributing to background noise.

As used herein, Neusilin™ is a synthetic, amorphous form of Magnesium Aluminometasilicate.

As used herein, povidone is polyvinylpyrrolidone polymer.

As used herein, Kollidon™ is Vinylpyrrolidone-vinyl acetate copolymer.

Figure 12:
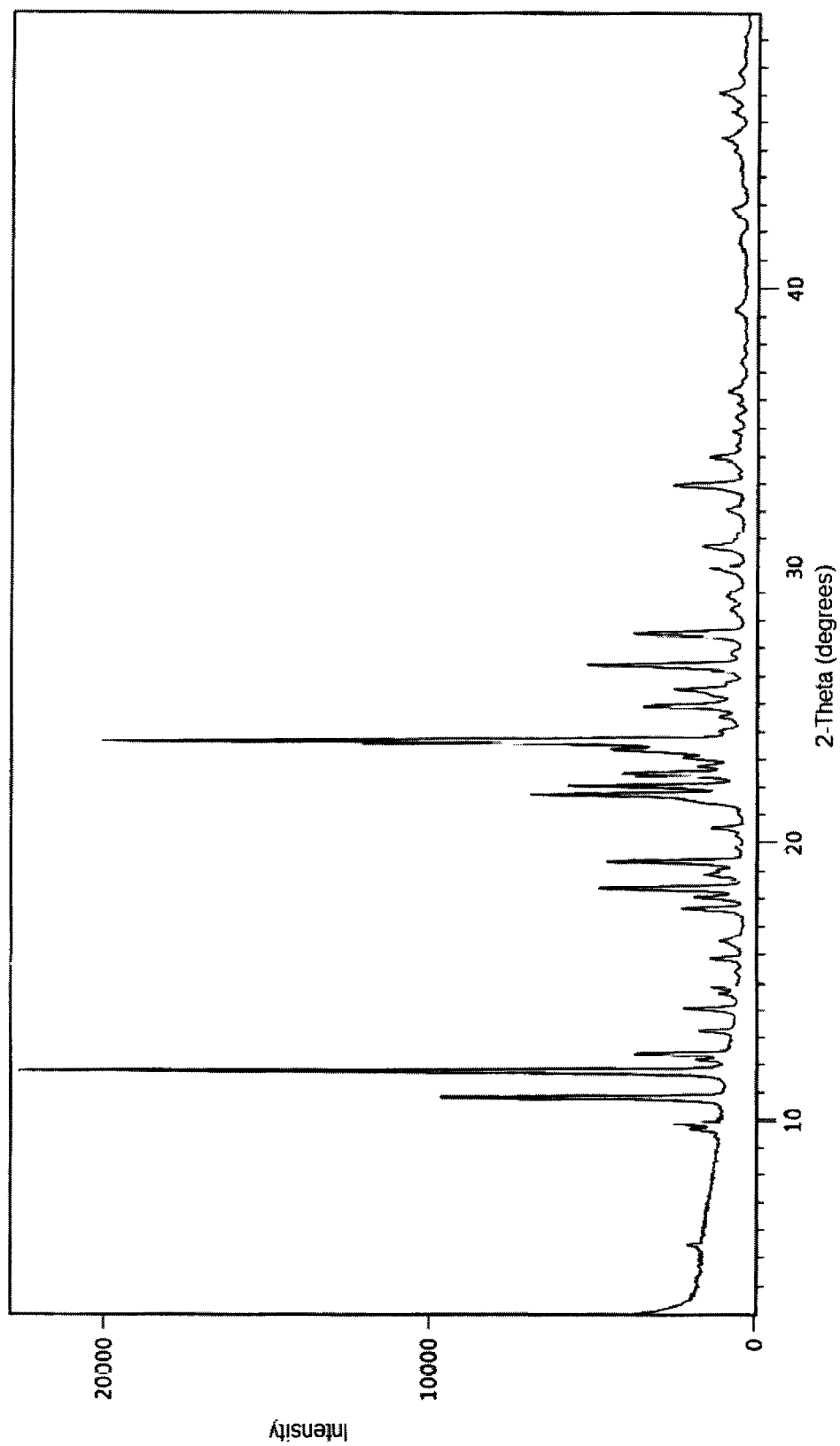
FIG. 12 is an illustration of a PXRD of Bosutinib Propylene glycol solvate, prepared according to Example 11.
Figure 13:
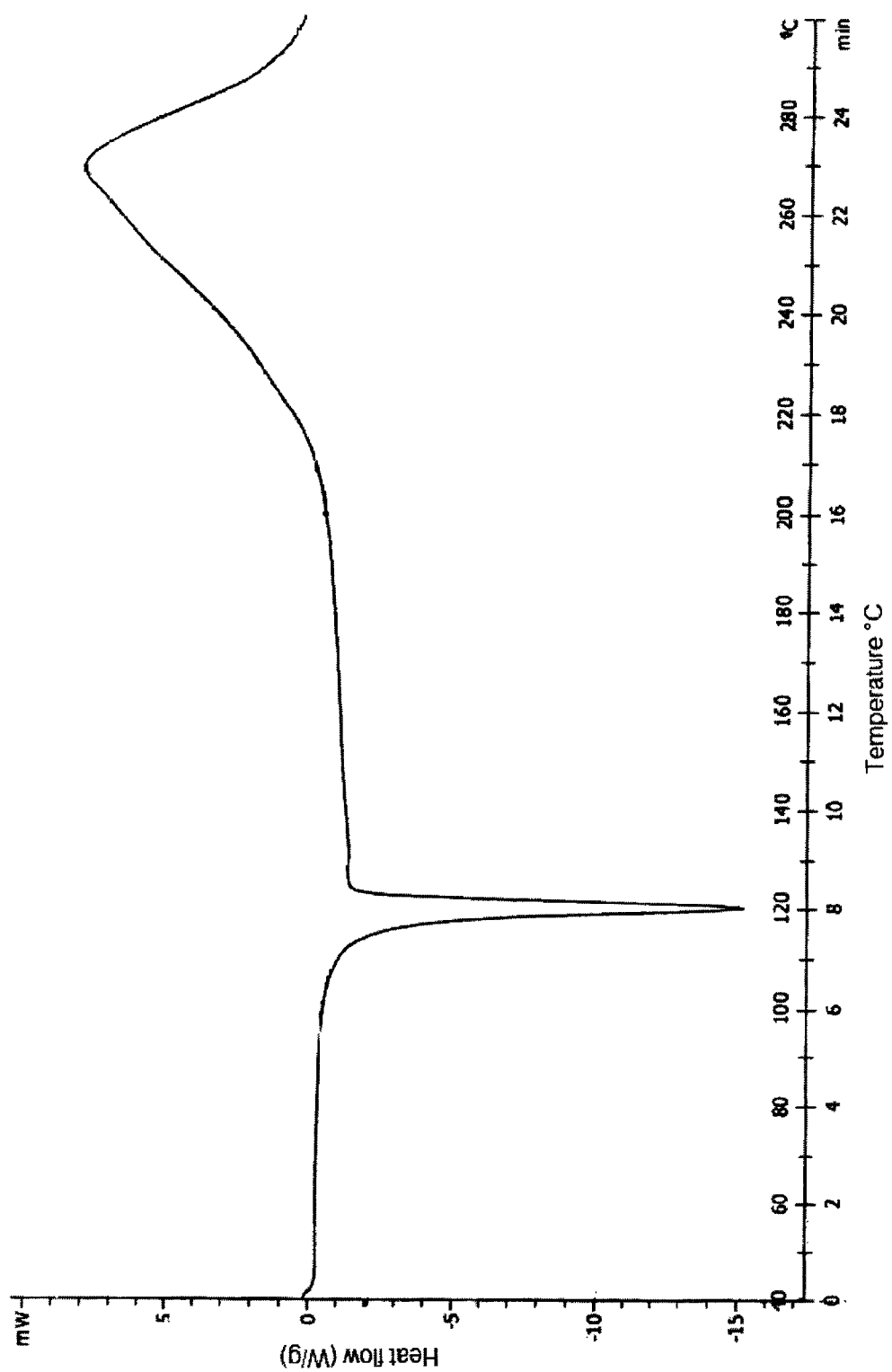
FIG. 13 is an illustration of a DSC curve of Bosutinib Propylene glycol solvate, prepared according to Example 11.

Illustrative embodiments of the present invention provide a propylene glycol solvate of Bosutinib. The propylene glycol solvate of Bosutinib may be characterized by a powder X-ray diffractogram (PXRD) comprising peaks, in terms of degrees 2-theta, at about 10.8±0.2°, 11.7±0.2°, 21.7±0.2°, and 23.6±0.2°. The PXRD may further comprise at least one peak, in terms of degrees 2-theta, selected from the group consisting of: 18.3±0.2°, 19.3±0.2°, 22.1±0.2°, and 26.3±0.2°. The PXRD may further comprise at least one peak, in terms of degrees 2-theta, selected from the group consisting of: 12.4±0.2°, 23.3±0.2°, 24.9±0.2°, and 27.5±0.2°. Illustrative embodiments of the present invention provide a crystalline propylene glycol solvate of Bosutinib characterized by a PXRD substantially similar to the PXRD as illustrated in FIG. 12. Illustrative embodiments of the present invention provide a crystalline propylene glycol solvate of Bosutinib characterized by a differential scanning calorimetry (DSC) thermogram substantially similar to the DSC thermogram as illustrated in FIG. 13. In aspects of the present invention, the (molar) ratio of Bosutinib to Propylene glycol in Bosutinib Propylene glycol solvate may range from about 1:0.5 to about 1:2 depending on a variety of conditions understood to a person of skill in the art.

Illustrative embodiments of the present invention provide a process for preparing propylene glycol solvate of Bosutinib. The process comprises:
 a) providing a solution or suspension of Bosutinib or solvate thereof in propylene glycol, thereby forming a reaction mixture;
 b) maintaining the reaction mixture at a suitable temperature, thereby forming a maintained reaction mixture; and
 c) isolating the propylene glycol solvate of Bosutinib from the maintained reaction mixture.

In embodiments of step a), any physical form of Bosutinib may be utilized for providing the solution of Bosutinib. Propylene glycol used may be in any stereochemical form, including (R), (S), racemic or any ratio of (R):(S) enantiomers. The racemic form of Propylene glycol is often used in the present invention.

Providing the solution or suspension of Bosutinib or solvate thereof in propylene glycol may further comprise providing the solution or suspension in a suitable solvent. The suitable solvent may be an organic solvent. Examples of suitable solvents that may be used in embodiments of step a), include, but are not limited to; alcohols, esters, ketones, hydrocarbons, ethers, nitriles, amides, water, and mixtures of at least two thereof. Further, suitable solvents may include, but are not limited to: alcohols, such as methanol, ethanol, 1-propanol and 2-propanol (isopropyl alcohol); ethers, such as diethyl ether, diisopropyl ether, methyl tertiary-butyl ether and tetrahydrofuran; esters, such as methyl acetate, ethyl acetate, propyl acetate and isopropyl acetate; halogenated hydrocarbons, such as dichloromethane; ketones, such as acetone, methyl ethyl ketone and methyl isobutyl ketone; and mixtures of at least two thereof.

In embodiments of step b), the reaction mixture may be maintained at a suitable temperature less than about 100° C., less than about 90° C. or less than about 80° C.

Illustrative embodiments of the present invention provide a pharmaceutical composition comprising a propylene glycol solvate of Bosutinib together with one or more pharmaceutically acceptable excipients, carriers, or diluents.

Figure 2:
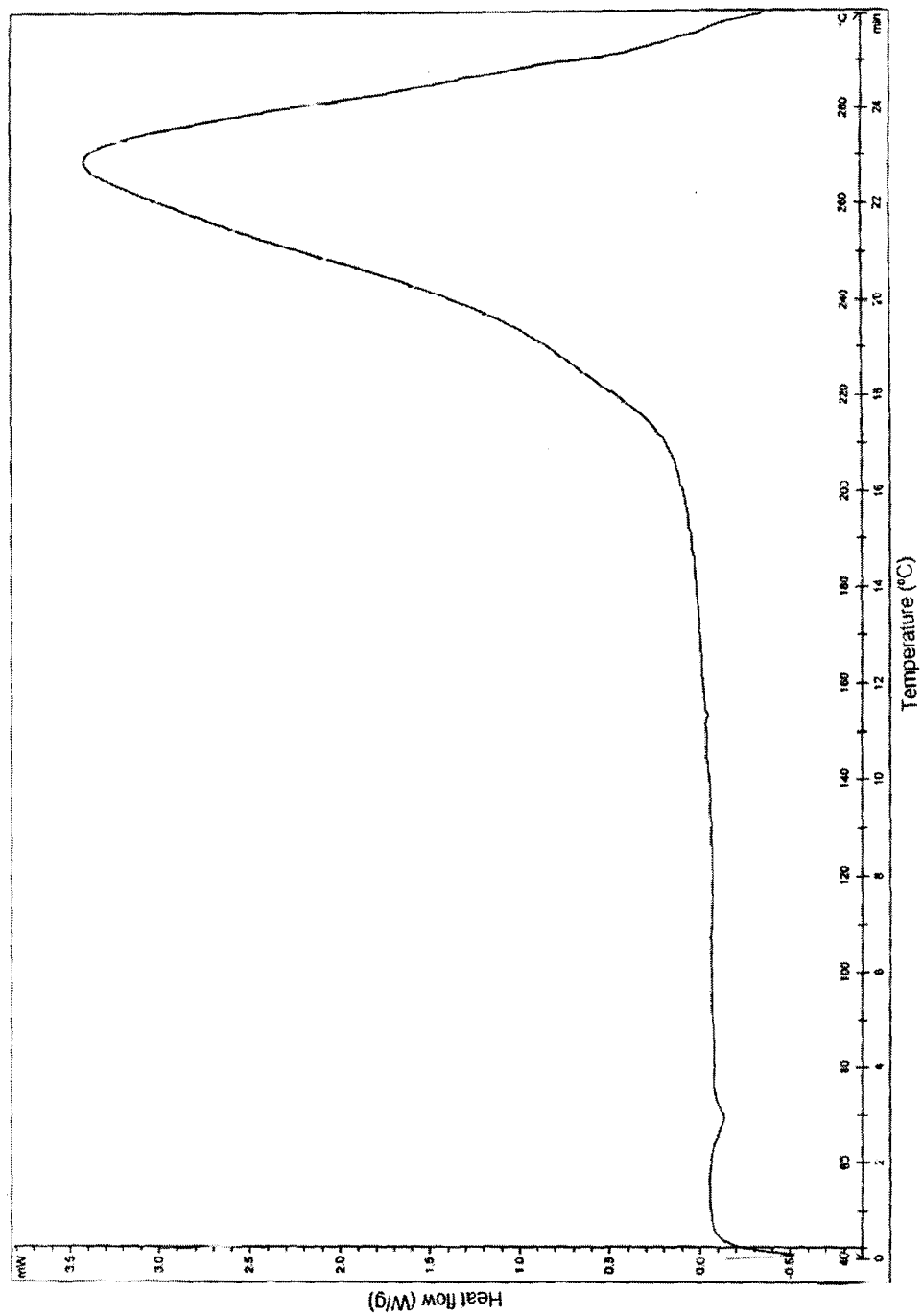
FIG. 2 is an illustration of a differential scanning calorimetry (DSC) curve of amorphous Bosutinib, prepared according to Example 5.
Figure 3:
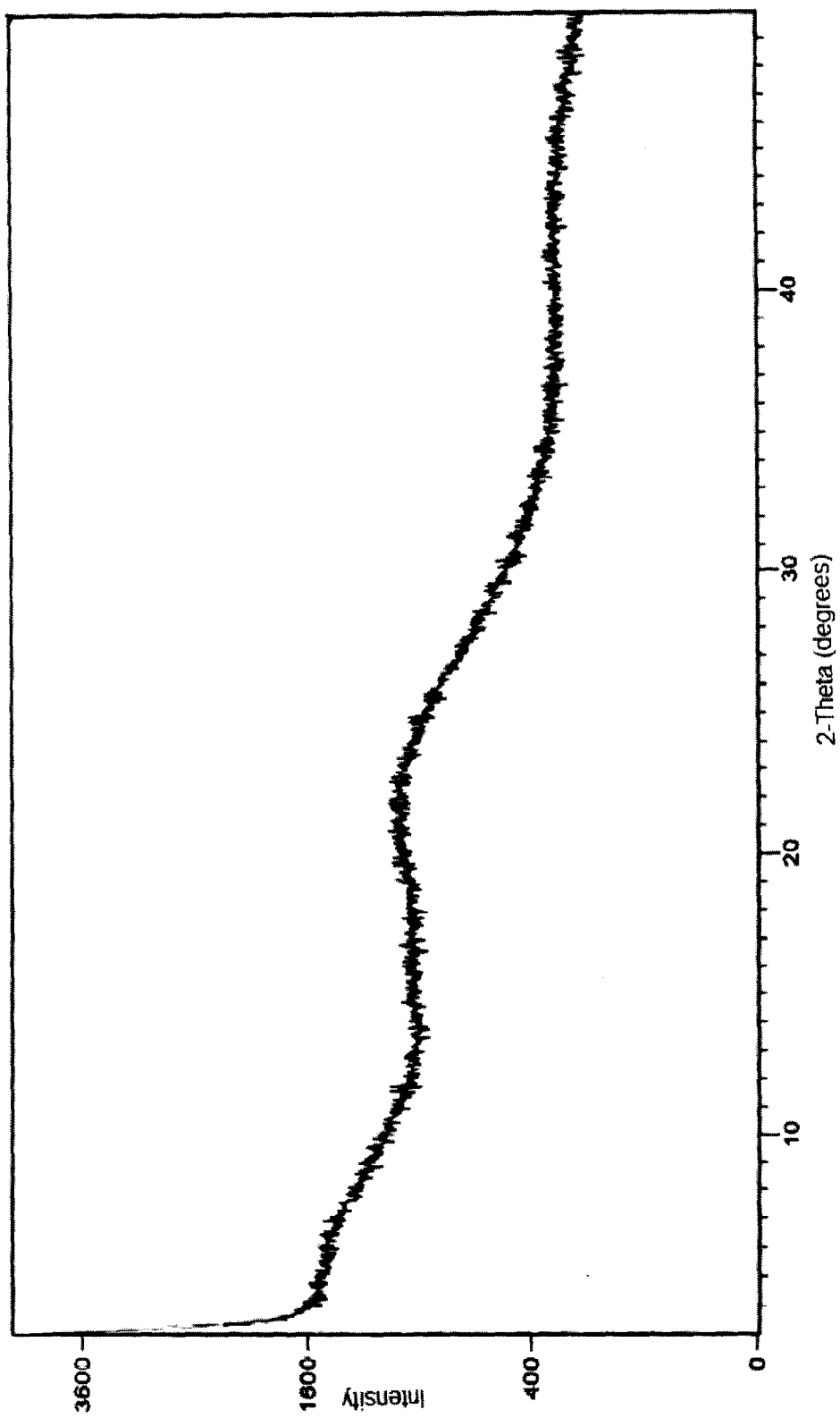
FIG. 3 is an illustration of a PXRD of amorphous Bosutinib, prepared according to Example 6.
Figure 4:
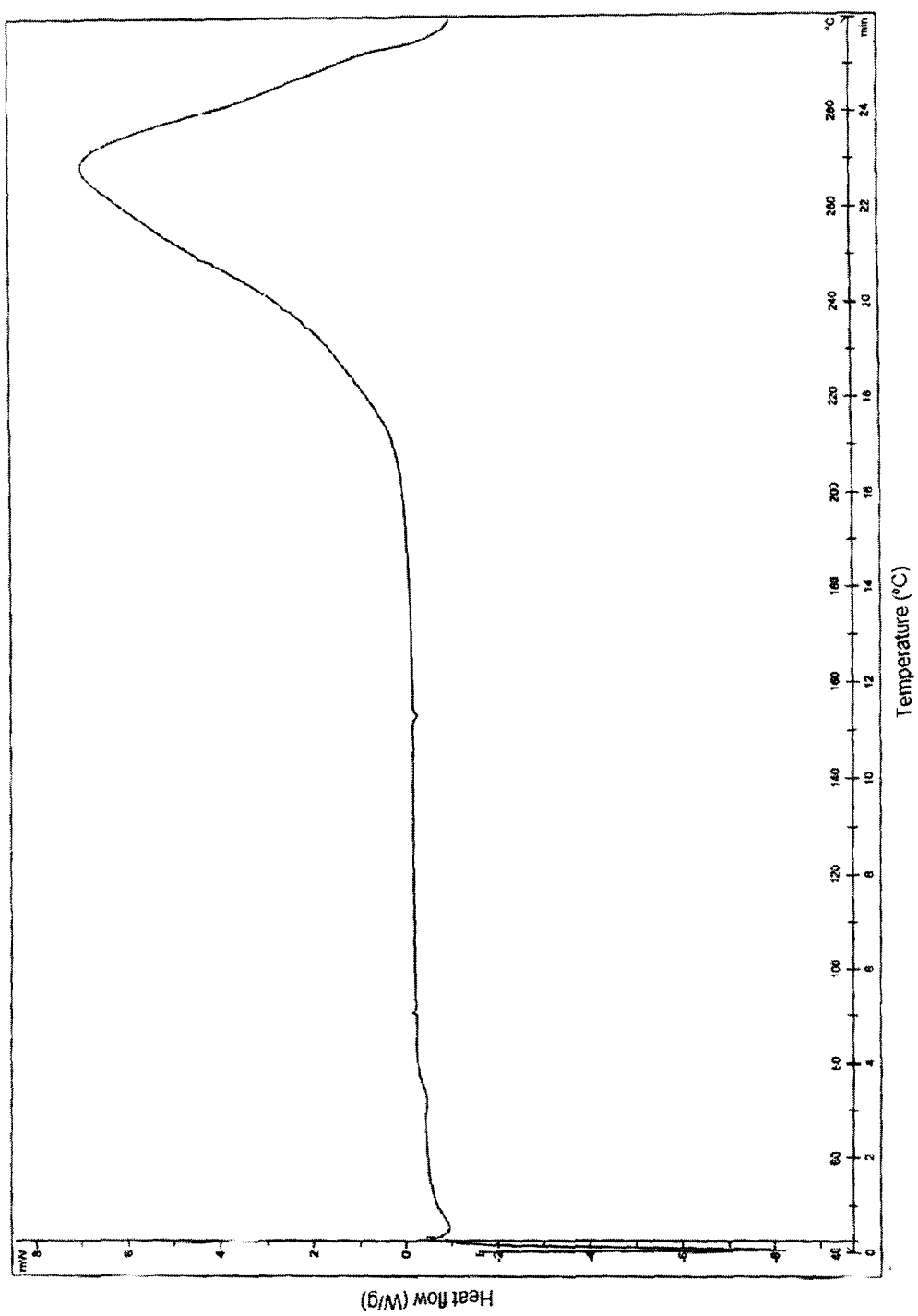
FIG. 4 is an illustration of a DSC curve of amorphous Bosutinib, prepared according to Example 6.
Figure 5:
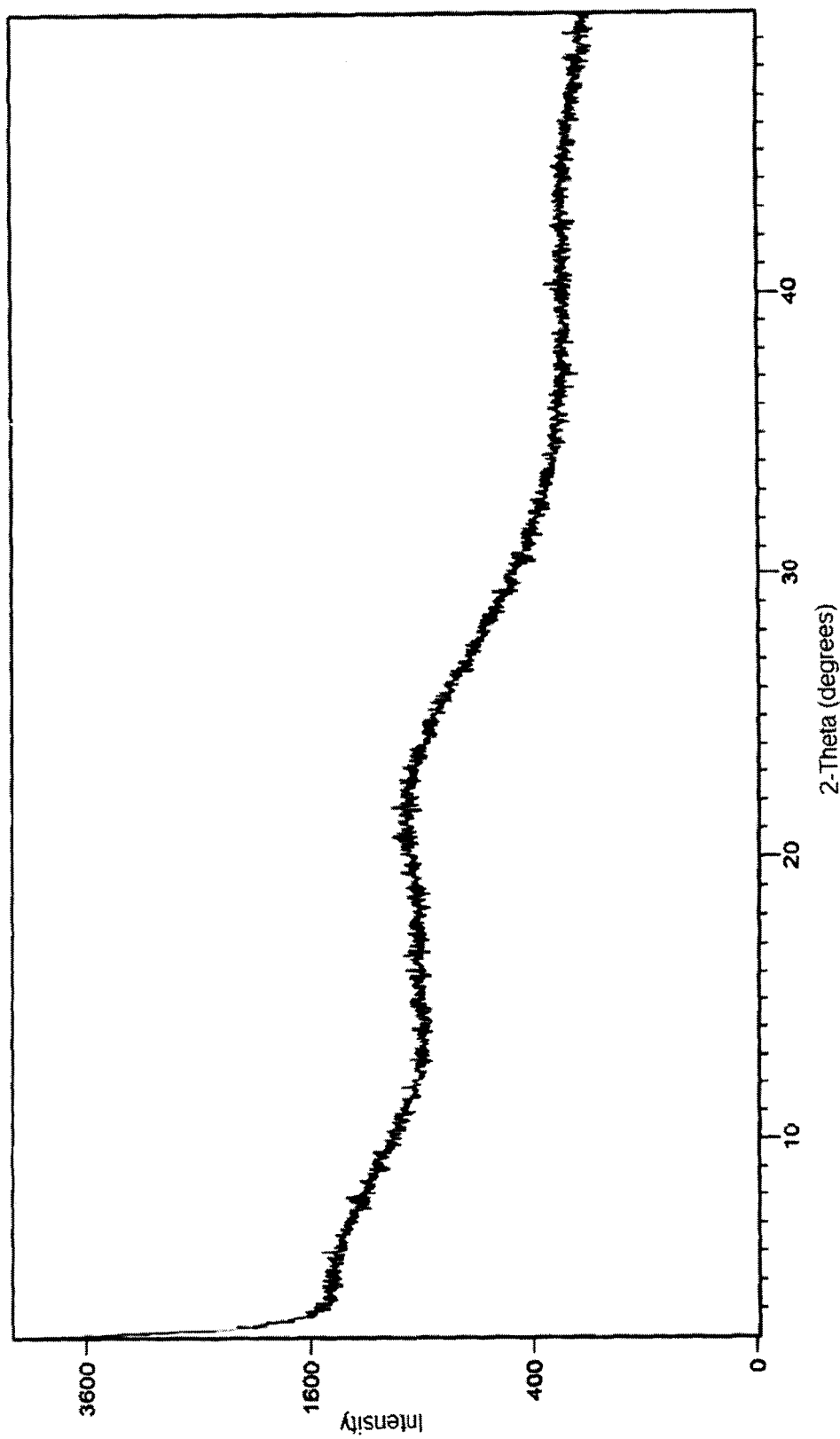
FIG. 5 is an illustration of a PXRD of amorphous Bosutinib, prepared according to Example 7.
Figure 6:
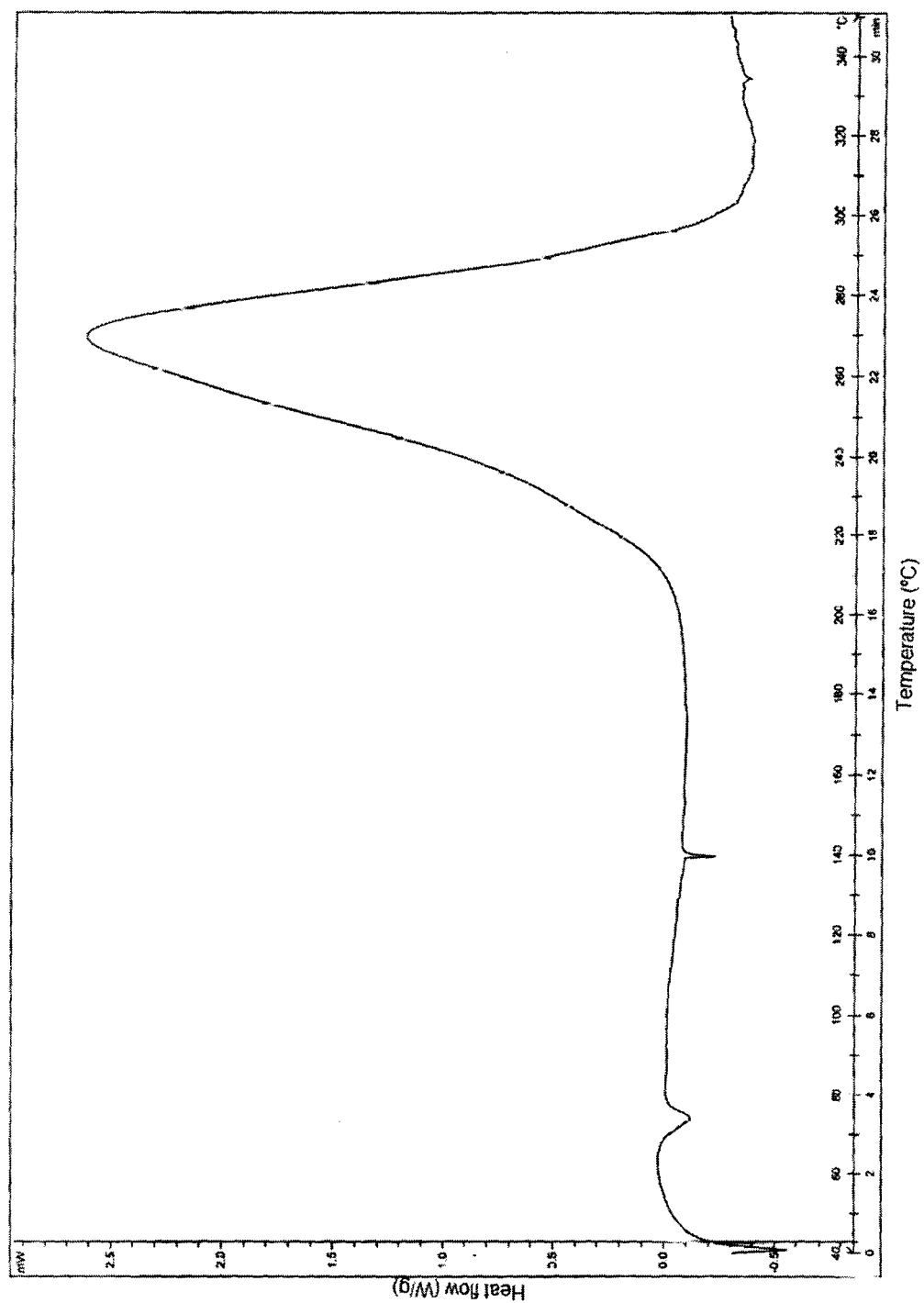
FIG. 6 is an illustration of a DSC curve of amorphous Bosutinib, prepared according to Example 7.

Illustrative embodiments of the present invention provide an amorphous form of Bosutinib. The amorphous form of Bosutinib may be substantially pure. The amorphous form of Bosutinib may be characterized by a PXRD as illustrated in any one of FIG. 1, 3, or 5. The amorphous form of Bosutinib may be characterized by a DSC thermogram as illustrated in any one of FIG. 2, 4, or 6.

Illustrative embodiments of the present invention provide a process for preparing an amorphous form of Bosutinib. The process comprises:

A) providing a solution of Bosutinib or solvate thereof in a solvent; and

B) isolating the amorphous form of Bosutinib from the solution.

Providing a solution of Bosutinib in step A) may include:

1) direct use of a reaction mixture containing Bosutinib that is obtained in the course of its synthesis which either comprises a suitable solvent, or may be combined with a suitable solvent; or 2) dissolving Bosutinib in a solvent.

Direct use of a reaction mixture in step A) may comprise using any process, including processes described in the art, that produce Bosutinib and the reaction mixture may optionally be purified by using any method known in the art to enhance the chemical purity of Bosutinib.

Providing a solution in step A) may comprise providing a solution in which Bosutinib is dissolved in a suitable solvent until a clear solution of Bosutinib is obtained. Any physical form of Bosutinib may be utilized for providing the solution of Bosutinib, for example, but not limited to, the Bosutinib solvate may be selected from the group consisting of: methanol, isopropanol, acetonitrile, and propylene glycol solvates.

When dissolving the Bosutinib or solvate thereof, the dissolution temperatures may range from about 0° C. to about the reflux temperature of the solvent. Often the dissolution temperature may be less than about 70° C., less than about 60° C., less than about 50° C., less than about 40° C., or any other suitable temperature. The solution may optionally be treated with carbon, flux-calcined diatomaceous earth (Hyflow), or any other suitable material to remove color, remove insoluble materials, improve clarity of the solution, and/or remove impurities that are adsorbable on such material. Optionally, the solution obtained may be treated to remove any insoluble particles. The insoluble particles may be removed suitably by filtration, centrifugation, decantation, or any other suitable techniques, under pressure or under reduced pressure. The solution may be filtered by passing through paper, glass fiber, cloth or other membrane material, or a bed of a clarifying agent such as Celite™ or Hyflow. Depending upon the concentration and temperature of the solution and the equipment used, the filtration apparatus may optionally be preheated to avoid premature crystallization.

Suitable solvents that may be used for providing a solution of Bosutinib in Step A) include, but are not limited to: alcohols, esters, ketones, hydrocarbons, ethers, nitriles, amides, water, and mixtures of at least two thereof. Further, suitable solvents may include, but are not limited to: alcohols, such as methanol, ethanol, 1-propanol, 2-propanol (isopropyl alcohol), 1-butanol, 2-butanol, iso-butyl alcohol, t-butyl alcohol, and $C_1$-$C_6$ alcohols; ethers, such as diethyl ether, diisopropyl ether, methyl tertiary-butyl ether, tetrahydrofuran, 2-methyltetrahydrofuran, cyclopropylmethyl ether, dioxane, and dimethoxyethane; esters, such as methyl acetate, ethyl formate, ethyl acetate, propyl acetate, isopropyl acetate, butyl acetate, and isobutyl acetate; halogenated hydrocarbons, such as dichloromethane; ketones, such as acetone, methyl ethyl ketone, methyl isobutyl ketone, and diethyl ketone; nitriles, such as acetonitrile and propionitrile; amides, such as formamide, N,N-dimethylformamide, and N,N-dimethylacetamide; sulfoxides, such as dimethylsulfoxide; and mixtures of at least two thereof.

Isolating the amorphous form of Bosutinib in step B) may be effected by removing the solvent, or by a precipitation technique. Suitable techniques that may be used for the removal of the solvent include using a rotational distillation device such as a Buchi™ Rotavapor™, spray drying, thin film drying, freeze drying, lyophilization, and the like, or any other suitable techniques.

The solvent may be removed, optionally under reduced pressures, at temperatures less than about 100° C., less than about 75° C., less than about 60° C., less than about 50° C., or any other suitable temperatures.

Freeze drying or lyophilisation may be carried out by freezing a solution of Bosutinib at low temperatures and reducing the pressure as required, to remove the solvent from the frozen solution of Bosutinib. Ideal temperatures to freeze the solution may range from about −80° C. to about 0° C., or up to about 20° C. and will depend on the solvent used to make the solution of Bosutinib. Ideal temperatures to remove the solvent from the frozen solution may be less than about 20° C., less than about 0° C., less than about −20° C., less than about −40° C., less than about −60° C., less than about −80° C., or any other suitable temperatures.

Isolation in step B) may also include combining the solution from step A) with a suitable anti-solvent. Adding the solution obtained from step A) to the anti-solvent, or adding an anti-solvent to the solution obtained from step A), to effect a precipitation are both suitable. Optionally, the combination with an anti-solvent may be carried out after concentrating the solution obtained from step A). Suitable anti-solvents that may be used include, but are not limited to: aliphatic or alicyclic hydrocarbon liquids; aromatic hydrocarbon liquids; ethers; and mixtures thereof.

The solid Bosutinib obtained from step B) may be collected using techniques such as for example, scraping, shaking the container, or other techniques that are suited to the equipment used. Optionally, the isolated solid Bosutinib may be further dried.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures. Drying may be carried out at temperatures less than about 100° C., less than about 60° C., less than about 50° C., less than about 20° C., less than about 0° C., less than about −20° C., or any other suitable temperature. The drying may be carried out for a time period suitable for obtaining a desired product quality, and is often from about 15 minutes to 24 hours, or longer.

The amorphous form of Bosutinib described herein may be formulated into a pharmaceutical composition comprising the amorphous form of Bosutinib together with one or more pharmaceutically acceptable excipients, carriers, or diluents. Further, the amorphous form of Bosutinib may be made into a solid dispersion comprising the amorphous form of Bosutinib together with one or more pharmaceutically acceptable excipients, carriers, or diluents. The solid dispersions may also be formulated into a pharmaceutical formulation comprising one or more pharmaceutically acceptable excipients, carriers, or diluents. The pharmaceutically acceptable carrier may comprise one or more of copovidone, povidone, or Neusilin™.

In some illustrative embodiments, the present invention provides solid dispersion of amorphous Bosutinib together with one or more pharmaceutically acceptable carriers, wherein at least about 10% of the Bosutinib is in amorphous form, or at least about 20%, or at least about 40%, or at least about 60%, or at least about 65%, or at least about 70%, or at least about 75%, or at least about 80%, or at least about 85%, or at least about 90%, or at least about 95%, or at least about 97.5%, or at least about 98%, or at least about 99%, or at least about 99.5% of the Bosutinib is in amorphous form.

Figure 9:
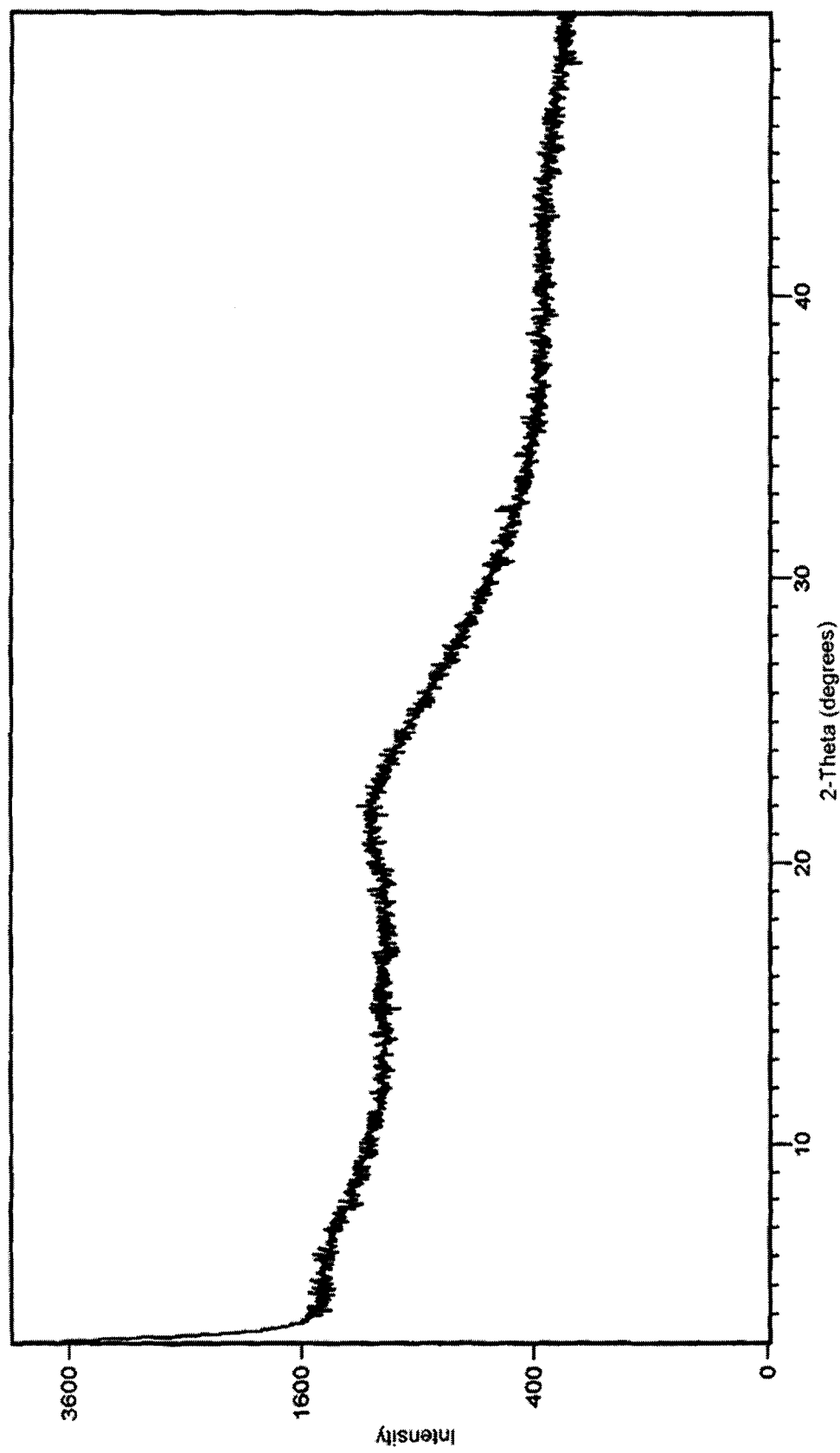
FIG. 9 is an illustration of a PXRD of solid dispersion of amorphous Bosutinib together with copovidone, prepared according to Example 8.

In illustrative embodiments of the present invention, there is provided a solid dispersion of amorphous Bosutinib together with copovidone. One such embodiment is characterized by a PXRD substantially as illustrated in FIG. 9.

Figure 10:
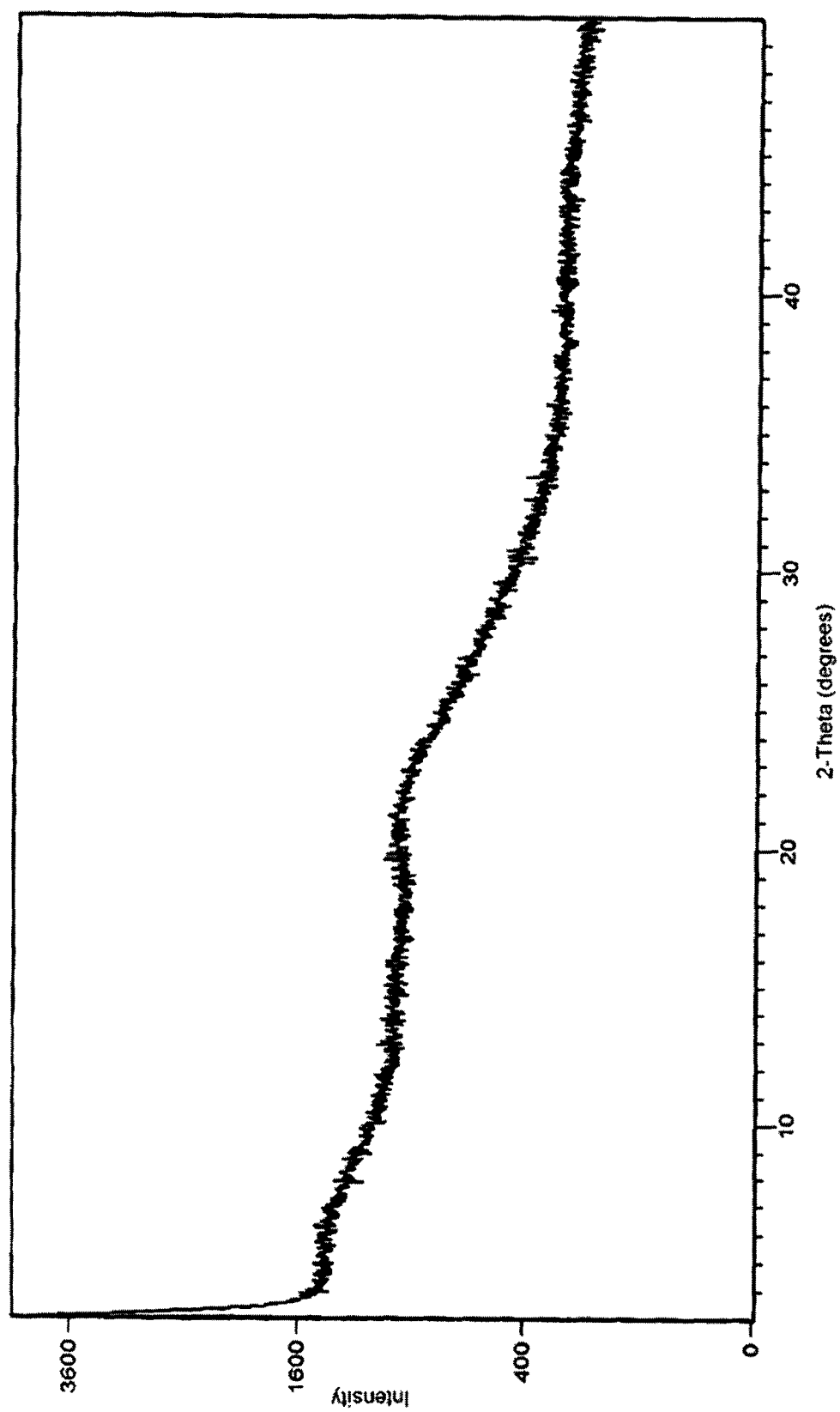
FIG. 10 is an illustration of a PXRD of solid dispersion of amorphous Bosutinib together with povidone, prepared according to Example 9.

In illustrative embodiments of the present invention, there is provided a solid dispersion of amorphous Bosutinib together with povidone. Once such embodiment is characterized by a PXRD substantially as illustrated in FIG. 10.

Figure 11:
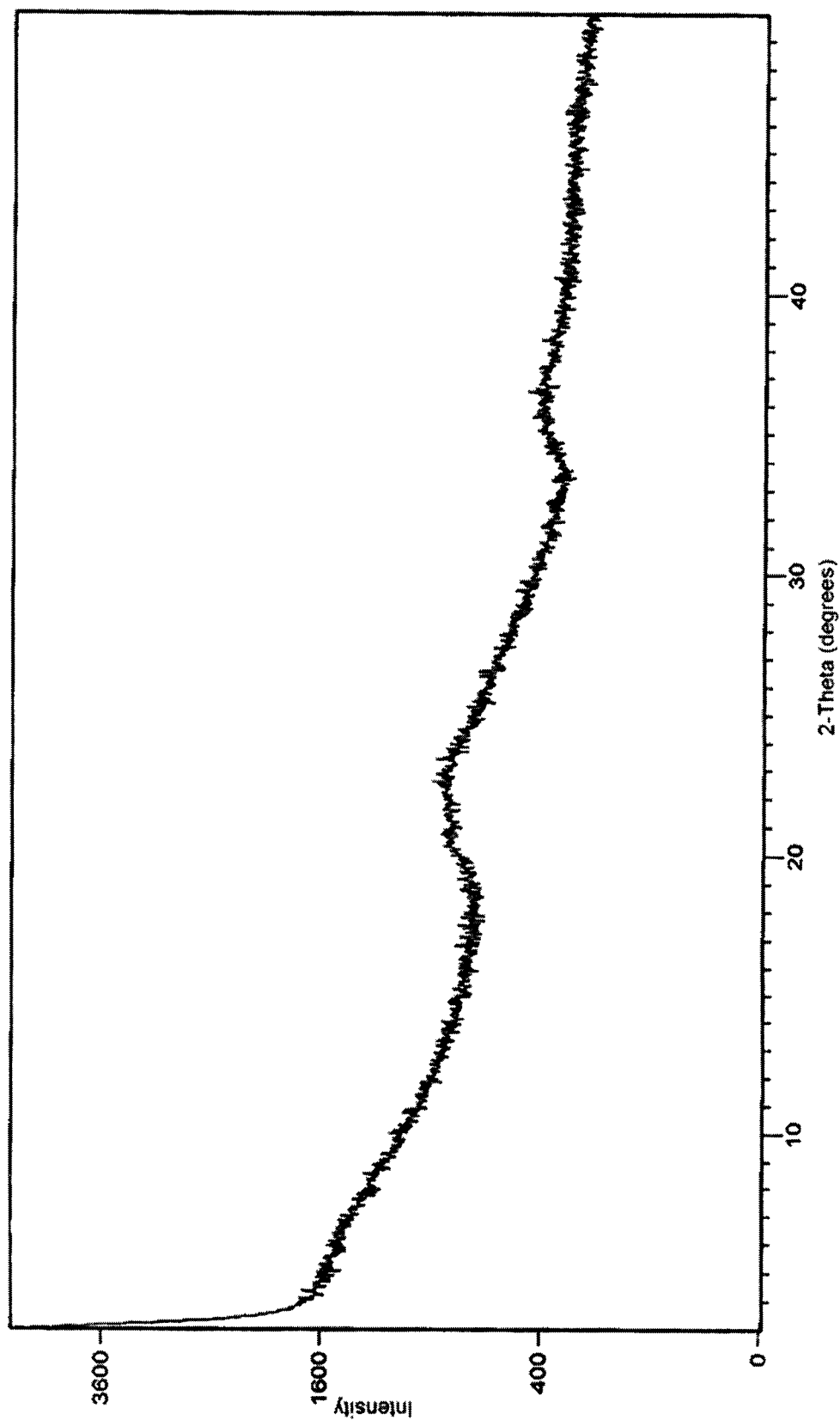
FIG. 11 is an illustration of a PXRD of solid dispersion of amorphous Bosutinib together with Neusilin™, prepared according to Example 10.

In illustrative embodiments of the present invention, there is provided a solid dispersion of amorphous Bosutinib together with Neusilin™. Once such embodiment is characterized by a PXRD substantially as illustrated in FIG. 11.

In illustrative embodiments of the present invention, there is provided a process for the preparation of a solid dispersion comprising an amorphous form of Bosutinib in combination with one or more pharmaceutically acceptable carriers. The process comprises:
  i) providing, in a solvent, a solution or a suspension comprising Bosutinib or a solvate thereof and one or more pharmaceutically acceptable carriers;
  ii) either:
    ii-i) removing the solvent from the solution or suspension; or
    ii-ii) combining the solution with an anti-solvent; and
  iii) isolating the solid dispersion comprising an amorphous form of Bosutinib in combination with one or more pharmaceutically acceptable carriers.

In embodiments of step i), providing a solution of Bosutinib may include direct use of a reaction mixture containing Bosutinib which reaction mixture is obtained in the course of the synthesis of Bosutinib and adding one or more pharmaceutically acceptable carriers. The reaction mixture may comprise a suitable solvent, or a suitable solvent may be added to the reaction mixture. The one or more pharmaceutically acceptable carriers may be added to the reaction mixture together with or separately from (before or after the addition of the suitable solvent to the reaction mixture) the suitable solvent.

Alternatively, embodiments of step i), may include providing a solution of Bosutinib by dissolving Bosutinib, or hydrate or solvate thereof, in a solvent, either alone or in combination with one or more pharmaceutically acceptable carriers. Examples of suitable solvates of Bosutinib include, but are not limited to methanol, isopropanol, acetonitrile, and propylene glycol solvates. The dissolution temperatures may range from about 0° C. to about the reflux temperature of the solvent, or less than about 100° C., less than about 70° C., less than about 60° C., less than about 50° C., or any other suitable temperatures, until a clear solution of Bosutinib is obtained. The solution may optionally be treated with carbon, flux-calcined diatomaceous earth (Hyflow), or any other suitable material to remove color, remove insoluble materials, improve clarity of the solution, and/or remove impurities that are adsorbable on such material.

Optionally, the solution obtained may be treated to remove any insoluble particles. The insoluble particles may be removed suitably by filtration, centrifugation, decantation, or any other suitable techniques, under pressure or under reduced pressure. The solution may be filtered by passing through paper, glass fiber, cloth or other membrane material, or a bed of a clarifying agent such as Celite™ or Hyflow. Depending upon the concentration and temperature of the solution and the equipment used, the filtration apparatus may optionally be preheated to avoid premature crystallization.

Pharmaceutically acceptable carriers that may be used for the preparation of solid dispersions of Bosutinib of the present invention include, but are not limited to: water soluble sugar derivatives including any pharmaceutically acceptable water soluble sugar excipients, preferably having low hygroscopicity, which include, but are not limited to, mannitol, lactose, fructose, sorbitol, xylitol, maltodextrin, dextrates, dextrins, lactitol, or the like; pharmaceutical hydrophilic carriers such as polyvinylpyrrolidones, gums, cellulose derivatives such as hydroxypropyl methylcelluloses, hydroxypropyl celluloses and microcrystalline celluloses, polymers of carboxymethyl celluloses, cyclodextrins, gelatins, hypromellose phthalates, sugars, polyhydric alcohols, polyethylene glycols, polyethylene oxides, polyoxyethylene derivatives, polyvinyl alcohols, propylene glycol derivatives, or the like; or organic amines such as primary, secondary, and tertiary alkyl amines, aromatic amines, alicyclic amines, cyclic amines, aralkyl amines, hydroxylamine or its derivatives, hydrazine or its derivatives, and guanidine or its derivatives; or copovidone, povidone and Neusilin™. The scope of the present invention without limitation includes, the use of mixtures of more than one of the pharmaceutical excipients to provide desired release profiles or for the enhancement of stability and also includes all viscosity grades, molecular weights, commercially available products, their copolymers and mixtures.

Suitable solvents used in embodiments of step i), include, but are not limited to: alcohols, esters, ketones, hydrocarbons, ethers, nitriles, amides, water, and mixtures of at least two thereof. Further, suitable solvents may include, but are not limited to: alcohols, such as methanol, ethanol, 1-propanol, 2-propanol (isopropyl alcohol), 1-butanol, 2-butanol, iso-butyl alcohol, t-butyl alcohol, and $C_1$-$C_6$ alcohols; ethers, such as diethyl ether, diisopropyl ether, methyl tertiary-butyl ether, tetrahydrofuran, 2-methyltetrahydrofuran, cyclopropylmethyl ether, dioxane, and dimethoxyethane; esters, such as methyl acetate, ethyl formate, ethyl acetate, propyl acetate, isopropyl acetate, butyl acetate, and isobutyl acetate; halogenated hydrocarbons, such as dichloromethane; ketones, such as acetone, methyl ethyl ketone, methyl isobutyl ketone, and diethyl ketone; nitriles, such as acetonitrile and propionitrile; amides, such as formamide, N,N-dimethylformamide, and N,N-dimethylacetamide; sulfoxides, such as dimethylsulfoxide; and mixtures of at least two thereof.

Suitable anti-solvents that may be used in embodiments of step ii) include, but are not limited to: aliphatic hydrocarbon liquids, alicyclic hydrocarbon liquids, aromatic hydrocarbon liquids, ethers, and mixtures of at least two thereof.

In other embodiments of step ii), removal of the solvent may be effected by using suitable techniques that include, but are not limited to, evaporation of the solvent, using a rotational distillation device such as a Buchi™ Rotavapor™, spray drying, thin film drying, freeze drying, lyophilisation, methods as mentioned herein, and the like, or any other suitable techniques. In some embodiments, the removing the solvent comprises evaporating the solvent, distilling, spray drying, thin film drying, freeze drying, lyophilisation, or a combination thereof. The solvent may be removed, optionally under reduced pressures, at temperatures less than about 100° C., less than about 75° C., less than about 60° C., less than about 50° C., or any other suitable temperature.

In embodiments of step iii), isolation may be effected by removing the solvent by techniques mentioned herein above, or by any other precipitation technique.

The solid obtained from step iii) may be collected using techniques such as for example, scraping, shaking the container, or other techniques that are suited to the equipment used. Optionally, the isolated solid may be further dried.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, at temperatures less than about 100° C., less than about 60° C., less than about 50° C., less than about 20° C., less than about 0° C., less than about −20° C., or any other suitable temperatures. The drying may be carried out for any time period suitable for obtaining a desired product quality, such as from about 15 minutes to 24 hours, or longer.

Examples of amorphous solid dispersions of Bosutinib in combination with one or more pharmaceutically acceptable carrier prepared according the processes described herein are characterized by a PXRD as illustrated in FIGS. 9, 10, and 11.

In some embodiments, a solid dispersion comprising an amorphous form of Bosutinib together with one or more pharmaceutically acceptable excipients, carriers, or diluents may be formulated into a pharmaceutical formulation.

Figure 7:
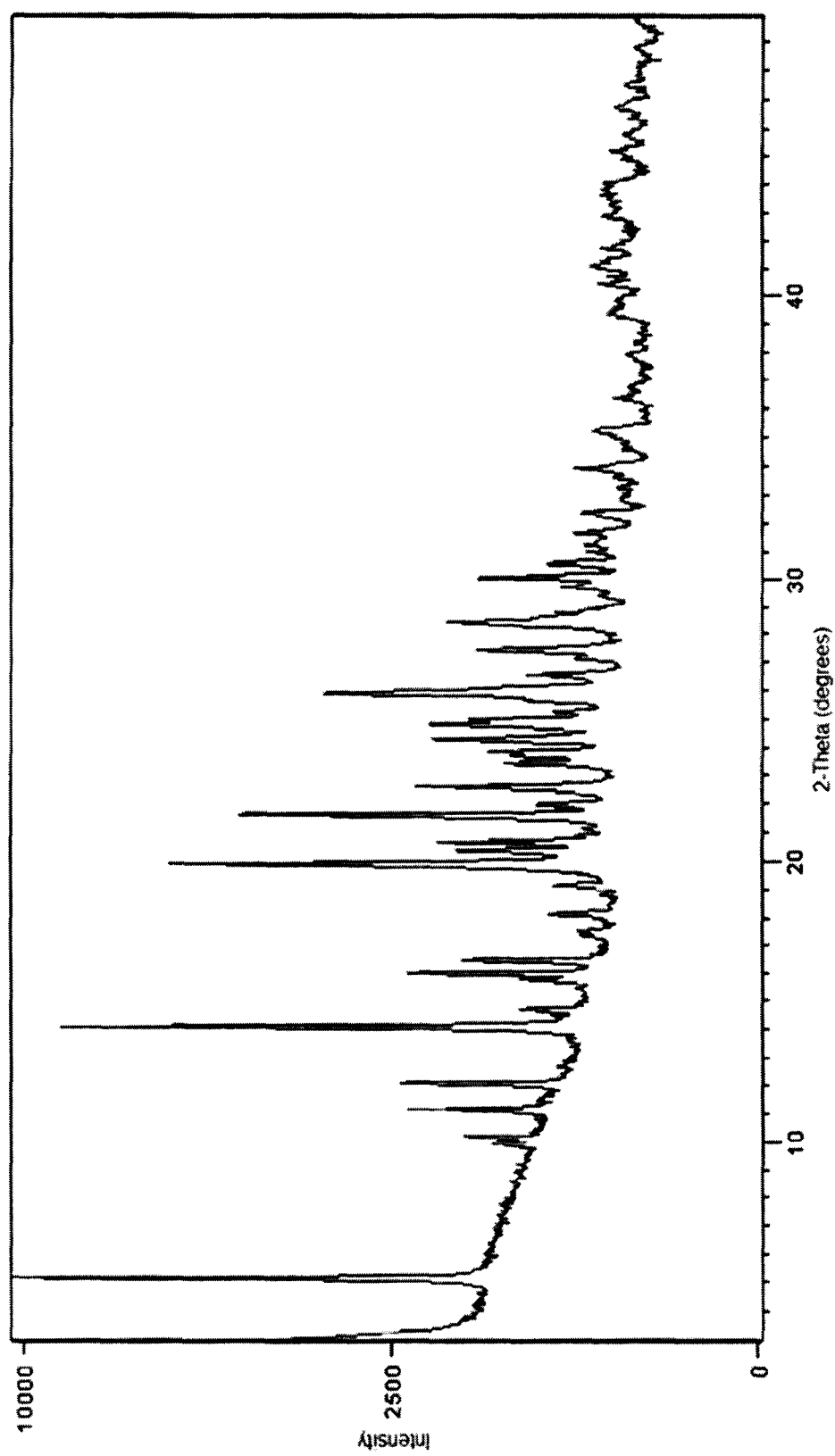
FIG. 7 is an illustration of a PXRD of Bosutinib acetonitrile solvate, prepared according to Example 4.
Figure 8:
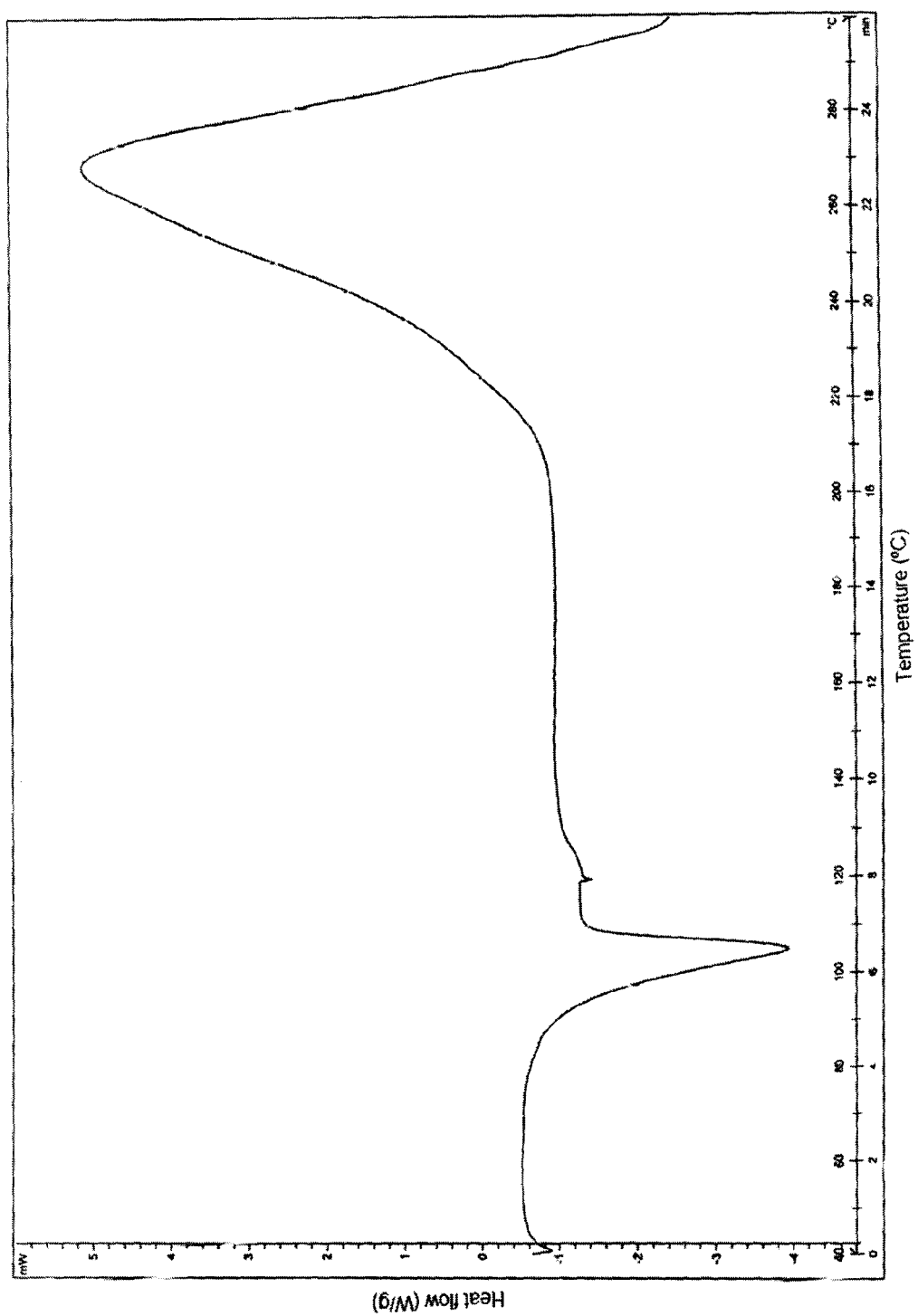
FIG. 8 is an illustration of a DSC curve of Bosutinib acetonitrile solvate, prepared according to Example 4.

In illustrative embodiments of the present invention, there is provided a crystalline acetonitrile solvate of Bosutinib. The crystalline acetonitrile solvate of Bosutinib may be characterized by a PXRD comprising peaks, in terms of degrees 2-theta, at about 5.1±0.2°, 14.1±0.2°, 19.9±0.2°, and 21.6±0.2°. Further, the PXRD may further comprise at least one peak, in terms of degrees 2-theta, selected from the group consisting of: 11.1±0.2°, 12.0±0.2°, 15.9±0.2°, and 20.6±0.2°. Further, the PXRD may further comprise at least one peak, in terms of degrees 2-theta, at about 22.6±0.2°, 24.2±0.2°, 24.7±0.2°, 25.9±0.2°, and 28.4±0.2°. One illustrative embodiment of a crystalline acetonitrile solvate of Bosutinib is characterized by a PXRD as illustrated in FIG. 7. One illustrative embodiment of a crystalline acetonitrile solvate of Bosutinib is characterized by a DSC thermogram as illustrated in FIG. 8. The (molar) ratio of Bosutinib to the acetonitrile solvate may range from about 1:0.5 to about 1:2 depending on a variety of conditions understood to a person of skill in the art.

Illustrative embodiments of the present invention provide a process for preparing a crystalline acetonitrile solvate of Bosutinib. The process may comprise:
  I) providing a solution or suspension of Bosutinib or solvate thereof in acetonitrile, thereby forming a reaction mixture;
  II) maintaining the reaction mixture at a suitable temperature, thereby forming a maintained reaction mixture; and
  III) isolating the crystalline acetonitrile solvate of Bosutinib from the maintained reaction mixture.

In embodiments of step I), any physical form of Bosutinib may be utilized for providing the solution of Bosutinib.

In embodiments of step II), the reaction mixture may be maintained at a suitable temperature less than about 100° C., less than about 90° C. or less than about 80° C.

In embodiments of step III), the isolating may comprise decantation, centrifugation, gravity filtration, suction filtration, concentrating, cooling, stirring, shaking, adding seed crystals, evaporation, or rotational drying.

In embodiments of the present invention, useful techniques for isolation, preferably for isolating Propylene glycol solvate and acetonitrile solvate of Bosutinib, include, but are not limited to, decantation, centrifugation, gravity filtration, suction filtration, concentrating, cooling, stirring, shaking, adding seed crystals, evaporation, rotational drying and the like. The isolation may be optionally carried out at atmospheric pressure or under a reduced pressure.

The isolated solid may be dried using any of an air tray dryer, vacuum tray dryer, fluidized bed dryer, spin flash dryer, flash dryer, and the like. The drying may be carried out at atmospheric pressure or above, or under reduced pressures, at temperatures less than about 100° C., less than about 60° C., less than about 50° C., less than about 20° C., less than about 0° C., less than about −20° C., or any other suitable temperatures. The drying may be carried out for any time period required for obtaining a desired product quality, such as from about 15 minutes to 24 hours, or longer.

In embodiments of the present invention, amorphous Bosutinib, Propylene glycol solvate of Bosutinib, acetonitrile solvate of Bosutinib and the solid dispersions of amorphous Bosutinib after optional drying, may be optionally further subjected to a particle size reduction procedure to produce desired particle sizes and distributions. Milling or micronization may be performed before drying, or after the completion of drying of the product. Equipment that may be used for particle size reduction include, without limitation thereto, ball mills, roller mills, hammer mills, and jet mills.

In an aspect of the invention, Bosutinib obtained according to certain processes of the present invention has a particle size distribution wherein: mean particle size is less than about 200 µm or less than about 100 µm; d (0.5) is less than about 200 µm or less than about 25 µm; and d (0.9) is less than about 500 µm or less than about 50 µm.

In aspects of the present invention, the amount of Bosutinib relative to the amount of pharmaceutically acceptable excipients, carriers, polymers or diluents present in the solid amorphous dispersions depends on the pharmaceutically acceptable excipients, carriers or diluents. Preferably, the ratio of Bosutinib to the pharmaceutically acceptable excipients, carriers, polymers or diluents ranges from about 1:0.5 to about 1:4.0.

In aspects of the present invention, Bosutinib or its solid state forms prepared according to the processes described herein are substantially pure, with a chemical purity greater than about 98%, or greater than about 99%, by weight, as determined using high performance liquid chromatography (HPLC).

Solid state forms of the present invention, including amorphous Bosutinib, propylene glycol solvate of Bosutinib, crystalline acetonitrile solvate of Bosutinib and the solid dispersions of amorphous Bosutinib with one or more pharmaceutical carriers, may be formulated as: solid oral dosage forms including, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization.

Compositions may be presented as uncoated, film coated, sugar coated, powder coated, enteric coated, and modified release coated.

Solid state forms of the present invention are stable, reproducible and amicable for large scale preparation. The present invention offers unique solubility and dissolution characteristics, which may enhance bioavailability of Bosutinib, which is a poorly water soluble drug.

EXAMPLES

The following examples are illustrative of some of the embodiments of the invention described herein. These examples do not limit the spirit or scope of the invention in any way.

Instrumentation

X-Ray Powder Diffraction (XRPD) Analysis

The data reported herein, were acquired on a PANanalytical X-pert Pro MPD diffractometer with fixed divergence slits and an X-Celerator RTMS detector. The diffractometer was configured in Bragg-Brentano geometry; data was collected over a 2θ range of 5 to 35 using CuKα radiation at a power of 30 mA and 45 kV. CuKβ radiation was removed using a divergent beam Nickel filter. A step size of 0.017 degrees was used. A step time of 50 seconds was used. The samples were prepared by the back-loading technique.

Differential Scanning Calorimetry (DSC) Analysis

The DSC thermograms reported herein, were collected on a Mettler-Toledo 822e instrument. Samples (1 to 3 mg) were weighed into a 40 μL aluminium pan and were crimped closed with an aluminium lid. The samples were analysed under a flow of nitrogen (ca. 50 mL/min) at a scan rate of 10° C. minute, from 40 to 350° C.

Example 1: Preparation of Crude Bosutinib Methanol Solvate 7-(3-Chloropropoxy)-4-(2,4-dichloro-5-methoxyphenylamino)-6-methoxyquinoline-3-carbonitrile (60 g) was taken in a round bottom flask and to this N,N-Dimethylformamide (180 mL) was added at 20-25° C. 1-Methylpiperazine (90 mL) was added to the reaction mixture at 20-25° C. The reaction mass was heated to 75-80° C., maintained for about 2 hours, then cooled to 20-30° C. and methanol (600 mL) was added at 20-30° C. The reaction mass was cooled to 0 to −5° C. and maintained for about 1.5 hours at 0 to −5° C. Solids were collected by filtration, washed with chilled methanol (120 mL) and were suck dried to afford the title compound. Yield: 70 g (wet)

Example 2: Preparation of Pure Methanol Solvate

Crude Bosutinib methanol solvate (28 g) was taken in a round bottom flask and to this, methanol (500 mL) was added at 25-30° C. The reaction mixture was heated to 60-65° C. and was maintained for 2 hours at 60-65° C. The reaction mass was cooled to 20-25° C. and maintained for 30 minutes at 20-25° C. Solids were collected by filtration, washed with methanol (56 mL) and dried in oven at 40-45° C. for about 8 hours to afford the title compound. Yield: 20.3 g; Purity by HPLC: 98.86% $^1$H NMR (DMSO-d6, 300 MHz) δ (ppm): 9.65 (s, 1H), 8.41 (s, 1H), 7.82 (s, 1H). 7.73 (s, 1H), 7.31 (s, 1H), 7.30 (s, 1H), 4.20-4.16 (t, 2H), 3.94 (s, 3H), 3.87 (s, 3H), 3.17 (s, 3H), 2.47-2.33 (m, 10H), 2.14 (s, 3H), 1.99-1.90 (m, 2H). $^{13}$C NMR (DMSO-d6, 75 MHz) δ (ppm): 153.96, 152.73, 150.57, 149.37, 149.31, 145.26, 136.74, 129.76, 122.79, 120.04, 116.94, 113.21, 112.62, 108.98, 101.92, 86.23, 66.84, 56.74, 56.16, 54.74, 54.26, 52.69, 48.56, 45.70, 25.97.

Example 3: Preparation of Bosutinib Isopropanol Solvate

Crude Bosutinib methanol solvate (23.3 g) was taken in a round bottom flask and to this isopropanol (116.5 mL) was added at 25-30° C. The reaction mixture was heated to 70-75° C., isopropanol (46.6 mL) was added at 70-75° C. and maintained for about 1 hour. The reaction mixture was cooled to 20-25° C., again maintained for about 1 hour at 20-25° C. and the reaction mixture was further cooled to 0-5° C. and maintained the same for 30 minutes. Solids were collected by filtration, washed with isopropanol (23.3 mL) and dried in vacuo for about 8 hours at 40-45° C. (Yield: 15.6 g)

The above obtained solid (15 g) was taken in a round bottom flask and to this isopropanol (180 mL) was added at 25-30° C. The reaction mass was heated to 75-80° C. and maintained for about 30 minutes at 75-80° C. Reaction mass was then cooled to 45-50° C. and was concentrated in vacuo at about 50° C. The resultant mass was co-distilled thrice with isopropanol (75 mL, 75 mL and 75 mL) at about 50° C. The resultant mass was cooled to 20-30° C., maintained for about 30 minutes, then further cooled to 0-5° C. and maintained for 30 minutes at 0-5° C. Solids were collected by filtration, washed with chilled isopropanol (15 mL) and dried in vacuo for about 8 hours at 40-45° C. to afford the title compound. Yield: 14.1 g; Purity by HPLC: 98.01% $^1$H NMR (DMSO-d6, 300 MHz) δ (ppm): 9.64 (s, 1H), 8.41 (s, 1H), 7.82 (s, 1H), 7.74 (s, 1H), 7.31 (s, 1H), 7.30 (s, 1H), 4.37-4.36 (d, 1H), 4.20-4.16 (t, 2H), 3.94 (s, 3H), 3.86 (s, 3H), 3.80-3.75 (m, 1H), 2.47-2.33 (m, 10H), 2.15 (s, 3H), 1.99-1.91 (m, 2H), 1.05-1.03 (d, 6H) $^{13}$C NMR (DMSO-d6, 75 MHz) δ (ppm): 153.96, 152.73, 150.54, 149.35, 149.30, 145.23, 136.64, 129.75, 122.80, 120.07, 116.93, 113.20, 112.60, 108.97, 101.91, 86.25, 66.83, 61.99, 56.73, 56.16, 54.71, 54.26, 52.66, 45.67, 25.97, 25.44

Example 4: Preparation of Crystalline Bosutinib Acetonitrile Solvate

Crude Bosutinib methanol solvate (23.3 g) was taken in a round bottom flask and to this acetonitrile (279.6 mL) was added at 20-30° C. The reaction mixture was heated to 50-55° C., maintained for 30 minutes and was concentrated in vacuo at about 50° C. The resultant mass was co-distilled twice with acetonitrile (233 mL and 233 mL), then the resultant mass was cooled to 20-25° C. and was maintained for about 1 hour at 20-25° C. Crystals were collected by filtration, washed with acetonitrile (23.3 mL) and dried in vacuo for about 8 hours at 40-45° C. (Yield: 14.5 g)

The above obtained crystals (12.5 g) were taken in a round bottom flask and to this acetonitrile (125 mL) was added at 20-25° C. The reaction mixture was heated to 75-80° C. and was maintained for 30 minutes at 75-80° C. The reaction mixture was then cooled to 20-30° C. and again maintained for about 1 hour. The crystals were collected by filtration, washed with acetonitrile (25 mL) and dried in vacuo for about 8 hours at 40-45° C. to afford the title compound. Yield: 10.4 g; Purity by HPLC: 98.97% $^1$H NMR (DMSO-d6, 300 MHz) δ (ppm): 9.65 (s, 1H), 8.41 (s, 1H), 7.82 (s, 1H), 7.73 (s, 1H), 7.32 (s, 1H), 7.30 (s, 1H), 4.20-4.16 (t, 2H), 3.95 (s, 3H), 3.87 (s, 3H), 2.46-2.33 (m, 10H), 2.14 (s, 3H), 2.08 (s, 3H), 1.97-1.90 (m, 2H) $^{13}$C NMR (DMSO-d6, 75 MHz) δ (ppm): 154.15, 152.91, 150.72, 149.54, 149.48, 145.50, 145.50, 136.94, 129.94, 122.98, 120.25, 118.17, 117.14, 113.37, 112.80, 109.16, 102.08, 86.45, 67.01, 56.90, 56.33, 54.91, 54.45, 52.87, 45.86, 26.17, 1.29. The PXRD pattern and DSC of crystalline Bosutinib acetonitrile solvate obtained is in accordance with FIGS. 7 and 8 respectively.

Example 5: Preparation of Amorphous Bosutinib

Crystalline Bosutinib acetonitrile solvate (9 g) was taken in a conical flask and to this acetone (90 mL) was added at 20-25° C. and stirred to obtain a clear solution. The clear solution was subjected to spray drying in vacuo at an inlet temperature of about 60° C. and then oven dried in vacuo at 45-50° C. for about 13 hours to afford the title compound. Yield: 7.8 g; Purity by HPLC: 98.86% The PXRD pattern and DSC of amorphous Bosutinib obtained is in accordance with FIGS. 1 and 2 respectively.

Example 6: Preparation of Amorphous Bosutinib

Bosutinib isopropanol solvate (10 g) was taken in a conical flask and to this acetone (100 mL) was added at 20-25° C. and stirred to obtain a clear solution. The clear solution was subjected to spray drying in vacuo at an inlet temperature of about 60° C. and then oven dried in vacuo at 40-45° C. for about 13 hours to afford the title compound. Yield: 8.5 g; Purity by HPLC: 98.43% The PXRD pattern and DSC of amorphous Bosutinib obtained is in accordance with FIGS. 3 and 4 respectively.

Example 7: Preparation of Amorphous Bosutinib

Bosutinib methanol solvate (10 g) was taken in a round bottom flask and to this acetone (100 mL) was added at 20-25° C. and stirred. The reaction mixture was heated to 30-35° C. to obtain a clear solution. The clear solution was subjected to spray drying in vacuo at an inlet temperature of about 60° C. and then oven dried in vacuo at 40-45° C. for about 13 hours to afford the title compound. Yield: 8.6 g; Purity by HPLC: 98.58% The PXRD pattern and DSC of amorphous Bosutinib obtained is in accordance with FIGS. 5 and 6 respectively.

Example 8: Preparation of Solid Dispersion of Amorphous Bosutinib with Copovidone (1:0.5)

Bosutinib methanol solvate (2 g) was taken in a Büchi™ flask and to this acetone (20 mL) was added at 20-25° C., followed by copovidone (1 g) (Kollidon™; VA64). The reaction mixture was heated to 55-60° C. and was concentrated in vacuo at about 55° C. The resultant mass was dried in vacuo at about 55° C. for 30 minutes to afford the title product. Yield: 2.6 g; The PXRD pattern of solid dispersion of amorphous Bosutinib with copovidone obtained is in accordance with FIG. 9.

Example 9: Preparation of Solid Dispersion of Amorphous Bosutinib with Povidone (1:0.5)

Bosutinib methanol solvate (1 g) was taken in a conical flask and to this acetone (10 mL) was added at 25-30° C., stirred to obtain a clear solution. To the reaction mixture povidone (0.5 g) (USP K30) was added at 25-30° C., followed by acetone (5 mL) and stirred to obtain a clear solution. The clear solution was subjected to spray drying with an inlet temperature of about 60° C. and the resultant material was dried in vacuo at about 60° C. for 15 minutes, to afford the title product. Yield: 0.9 g; The PXRD pattern of solid dispersion of amorphous Bosutinib with povidone obtained is in accordance with FIG. 10.

Example 10: Preparation of Solid Dispersion of Amorphous Bosutinib with Neusilin™ (1:0.5)

Bosutinib methanol solvate (1 g) was taken in a Büchi™ flask and to this Neusilin™ (0.5 g) (US2) was added, followed by acetone (30 mL) at 20-25° C. and stirred. The reaction mixture was heated to 50-55° C., maintained for 15 minutes at 50-55° C. and was concentrated in vacuo at about 50° C. The resultant material was dried in vacuo at 50-55° C. for about 1 hour to afford the title product. Yield: 1.2 g The PXRD pattern of solid dispersion of amorphous Bosutinib with povidone obtained is in accordance with FIG. 11.

Example 11: Preparation of Crystalline Propylene Glycol Solvate of Bosutinib Bosutinib methanol solvate (10 g) was taken in a round bottom flask and to this propylene glycol (20 mL) was added, followed by acetone (70 mL). The reaction mixture was heated to 55-60° C. and maintained for 1 hour at 55-60° C. The reaction mixture was cooled to 5-10° C. and maintained for 1 hour at 5-10° C. The solids were collected by filtration, washed with acetone (20 mL), suck dried and further dried in Buchi flask in vacuo for 12-13 hours at 45-50° C. to afford the title product. Yield: 9.2 g; Purity by HPLC: 99.83% $^1$H NMR (DMSO-d6, 300 MHz) δ (ppm): 9.63 (s, 1H), 8.40 (s, 1H), 7.81 (s, 1H), 7.72 (s, 1H), 7.32 (s, 1H), 7.28 (s, 1H), 4.45 (m, 2H), 4.18-4.14 (t, 2H), 3.94 (s, 3H), 3.87 (s, 3H), 3.62-3.52 (m, 1H), 3.29-3.24 (m, 1H), 3.19-3.14 (m, 1H), 2.45-2.31 (m, 10H), 2.13 (s, 3H), 1.99-1.90 (m, 2H), 1.01-0.99 (d, 3H)$^{13}$C NMR (DMSO-d6, 75 MHz) δ (ppm): 154.46, 153.22, 151.03, 149.85, 149.79, 145.77, 137.23, 130.25, 123.29, 120.56, 117.44, 113.68, 113.11, 109.46, 102.40, 86.74, 67.74, 67.67, 67.32, 57.22, 56.64, 55.23, 54.76, 53.17, 46.18, 26.48, 20.42 The PXRD pattern and DSC of crystalline Propylene glycol solvate of Bosutinib is in accordance with FIGS. 12 and 13 respectively.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A crystalline propylene glycol solvate of Bosutinib.

2. The crystalline propylene glycol solvate of Bosutinib of claim 1, wherein a powder X-ray diffractogram (PXRD) of the crystalline propylene glycol of Bosutinib comprises peaks, in terms of degrees 2-theta, at about 10.8±0.2°, 11.7±0.2°, 21.7±0.2°, and 23.6±0.2°.

3. A process for preparing a crystalline propylene glycol solvate of Bosutinib, comprising:
  a) providing a solution or suspension of Bosutinib or a solvate thereof in propylene glycol, thereby forming a reaction mixture;
  b) maintaining the reaction mixture at a suitable temperature, thereby forming a maintained reaction mixture; and
  c) isolating the propylene glycol solvate of Bosutinib from the maintained reaction mixture.

4. The process of claim 3, wherein providing the solution or suspension of Bosutinib or solvate thereof in propylene glycol further comprises providing the solution or suspension in a suitable solvent, wherein the suitable solvent is selected from the group consisting of: methyl acetate, ethyl acetate, propyl acetate, isopropyl acetate, acetone, methyl ethyl ketone, methyl isobutyl ketone, and mixtures of at least two thereof.

5. The crystalline propylene glycol solvate of Bosutinib of claim 2, wherein the powder X-ray diffractogram (PXRD) further comprises at least one peak, in terms of degrees 2-theta, selected from the group consisting of: 18.3±0.2°, 19.3±0.2°, 22.1±0.2°, and 26.3±0.2°.

6. The crystalline propylene glycol solvate of Bosutinib of claim 5, wherein the powder X-ray diffractogram (PXRD) further comprises at least one peak, in terms of degrees 2-theta, selected from the group consisting of: 12.4±0.2°, 23.3±0.2°, 24.9±0.2°, and 27.5±0.2°.

7. The crystalline propylene glycol solvate of Bosutinib of claim 2, wherein the powder x-ray diffractogram (PXRD) is substantially similar to the PXRD as illustrated in FIG. 12.

8. The crystalline propylene glycol solvate of Bosutinib of claim 2, wherein a DSC thermogram of the propylene glycol solvate of Bosutinib is substantially similar to the DSC thermogram as illustrated in FIG. 13.

9. The process of claim 4, wherein the suitable solvent is selected from the group consisting of: alcohols, esters, ketones, hydrocarbons, ethers, nitriles, amides, water, and mixtures of at least two thereof.

10. The process of claim 9, wherein the suitable solvent is selected from the group consisting of: methyl acetate, ethyl acetate, propyl acetate, isopropyl acetate, acetone, methyl ethyl ketone, methyl isobutyl ketone, and mixtures of at least two thereof.

11. A pharmaceutical composition comprising the propylene glycol solvate of Bosutinib of claim 2, together with one or more pharmaceutically acceptable excipients, carriers, or diluents.

* * * * *